(12) United States Patent
Ries et al.

(10) Patent No.: US 7,638,625 B2
(45) Date of Patent: Dec. 29, 2009

(54) CRYSTALLINE COMPOUNDS

(75) Inventors: Uwe Ries, Biberach (DE); Guenther Huchler, Hochdorf (DE); Sonja Sproll, Steinhausen a.d. Rottum/Englisweiler (DE); Ulrike Werthmann, Biberach (DE); Andreas Zopf, Ehingen/Risstissen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 192 days.

(21) Appl. No.: 11/734,520

(22) Filed: Apr. 12, 2007

(65) Prior Publication Data
US 2008/0086003 A1 Apr. 10, 2008

(30) Foreign Application Priority Data
Apr. 13, 2006 (DE) .................. 10 2006 017 827

(51) Int. Cl.
*C07D 491/04* (2006.01)
*C07D 491/14* (2006.01)
(52) U.S. Cl. .................................. 540/500
(58) Field of Classification Search ............ 540/500
See application file for complete search history.

(56) References Cited

U.S. PATENT DOCUMENTS 6,344,449 B1   2/2002   Rudolf et al.

FOREIGN PATENT DOCUMENTS

| CA | 2262818 A1 | 3/1998 |
| CA | 2503455 A1 | 5/2004 |
| CA | 2503462 A1 | 5/2004 |
| CA | 2558889 A1 | 10/2005 |
| WO | 9811128 A1 | 3/1998 |
| WO | 2004037810 A1 | 5/2004 |
| WO | 2004037811 A1 | 5/2004 |
| WO | 2005092880 A1 | 10/2005 |

OTHER PUBLICATIONS

Caira; Crystalline Polymorphism of Organic Compounds; Topics in Current Chemistry; 1998; Springer; Berlin, Germany; Bd. 198; pp. 163-208.
International Search Report, Form PCT/ISA/210, for corresponding PCT/EP2007/053488.

*Primary Examiner*—Bruck Kifle
(74) *Attorney, Agent, or Firm*—Michael P. Morris; Mary-Ellen M. Devlin; Alan R. Stempel

(57) ABSTRACT

The present invention relates to the new crystalline compounds A of general formula I

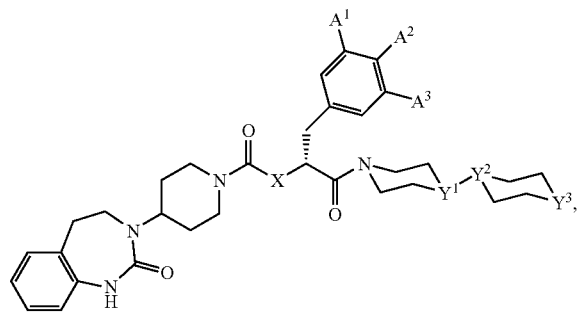

wherein $A^1, A^2, A^3, X, Y^1, Y^2$ and $Y^3$ are defined as in claim 1, and which are present in the form of their physiologically acceptable salts with acids, the acids being selected from the group B comprising hydrochloric acid, hydrobromic acid, sulphuric acid, phosphoric acid, benzenesulphonic acid, p-toluenesulphonic acid, maleic acid, succinic acid, fumaric acid, D-(−)-tartaric acid, L-(+)-tartaric acid, naphthalene-2-sulphonic acid and naphthalene-1,5-disulphonic acid, and the polymorphs, the corresponding solvates and hydrates thereof.

27 Claims, 14 Drawing Sheets

Figure 1: X-Ray powder diffractogram of the crystalline compound 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine-p-toluenesulphonate (1a).

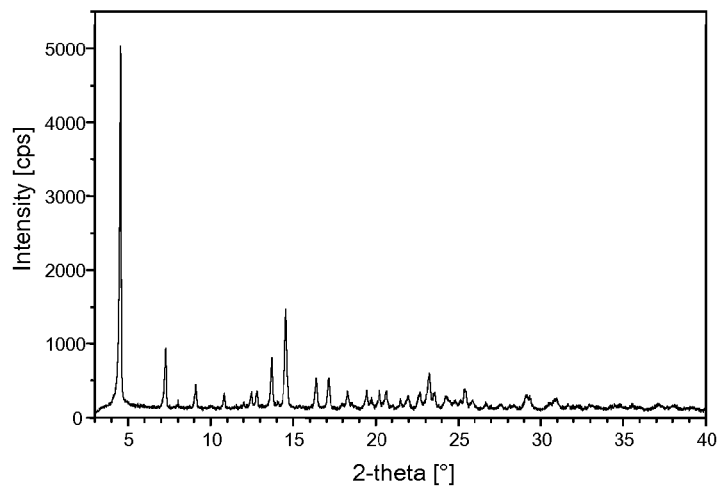

Figure 2: X-Ray powder diffractogram of the crystalline compound 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine-benzenesulphonate (1b).

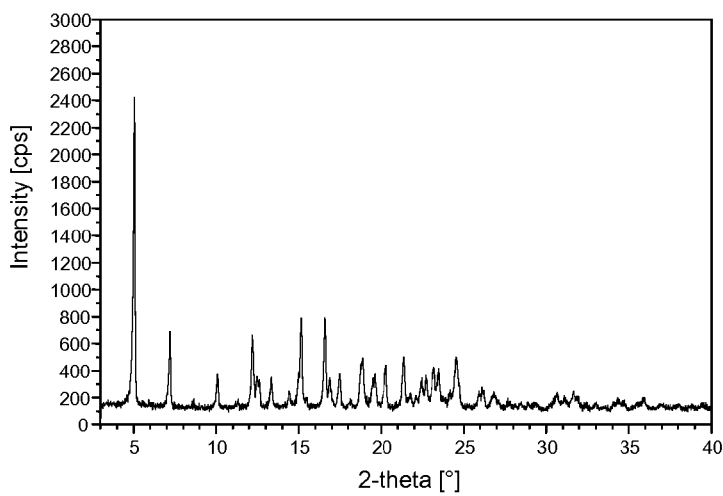

Figure 3: X-Ray powder diffractogram of the crystalline compound 1-[4-amino-3,5-dibromo-*N*-[[4-(2,3,4,5-tetrahydro-2(1*H*)-oxo-1,3-benzodiazepin-3-yl)-1-piperidinyl]carbonyl]-D-phenylalanyl]-4-(1-piperidinyl)-piperidine-maleate (1c).

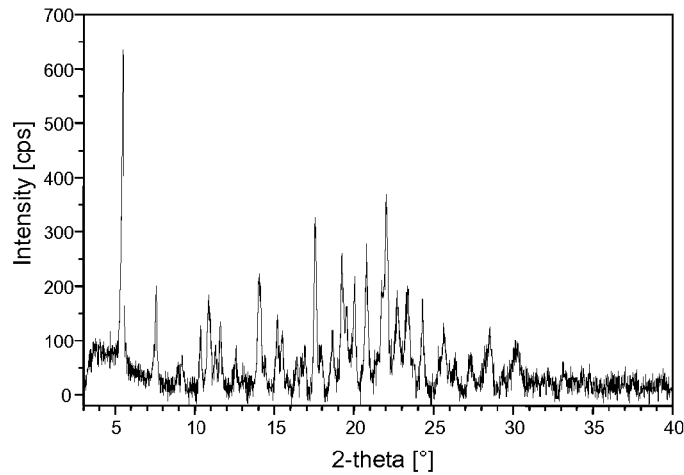

Figure 4: X-Ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dimaleate (2a).

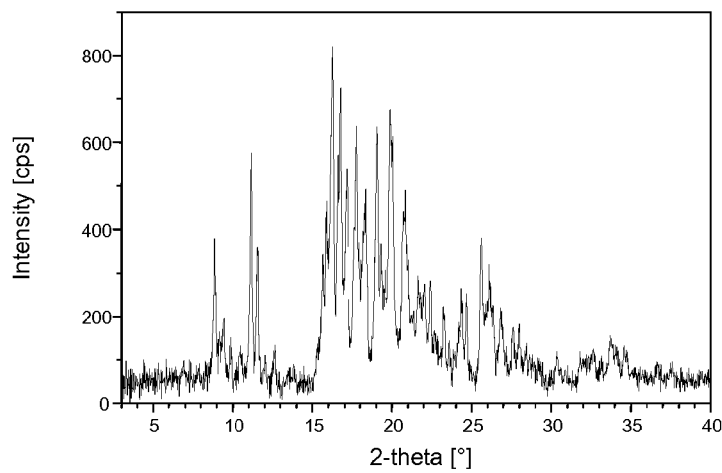

Figure 5: X-Ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrobromide (2b).

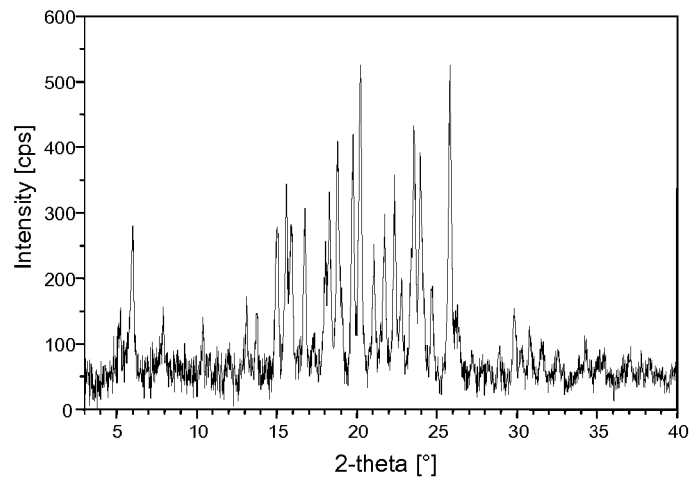

Figure 6: X-Ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dihydrobromide (2c).

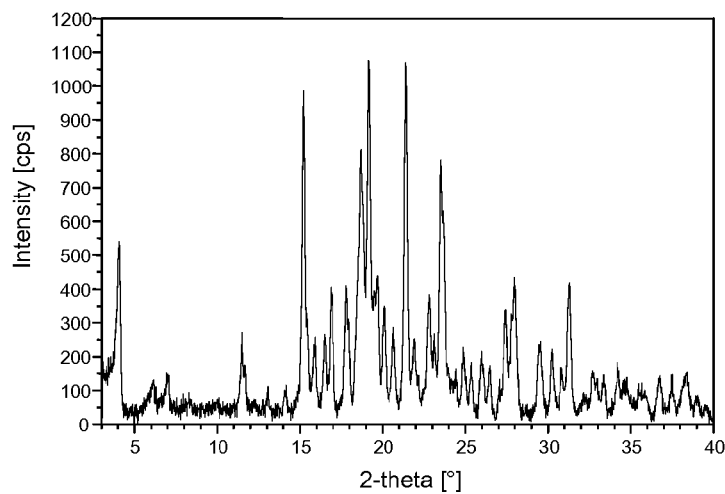

Figure 7: X-Ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrochloride (2d).

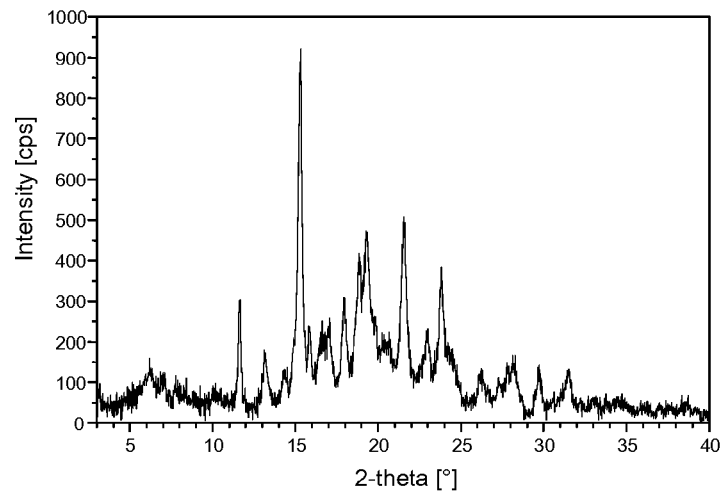

Figure 8: X-Ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate difumarate (2e).

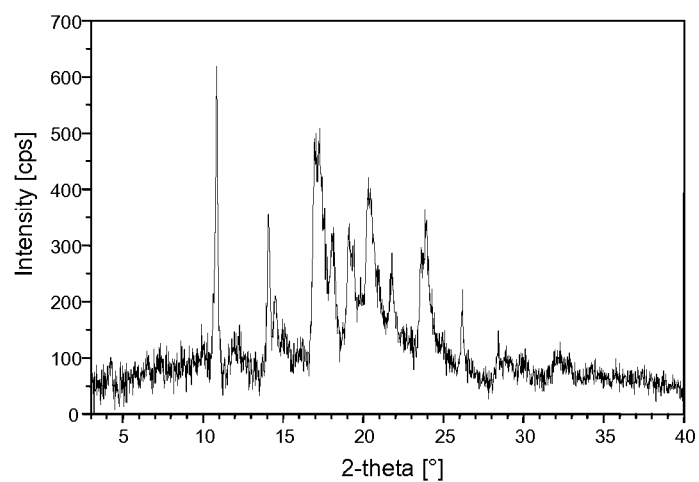

Figure 9: X-Ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate disuccinate (2f).

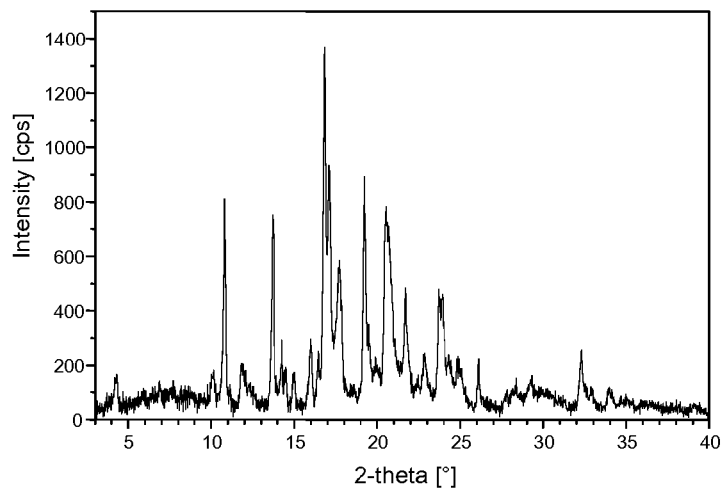

Figure 10: X-Ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate sulphate (2g).

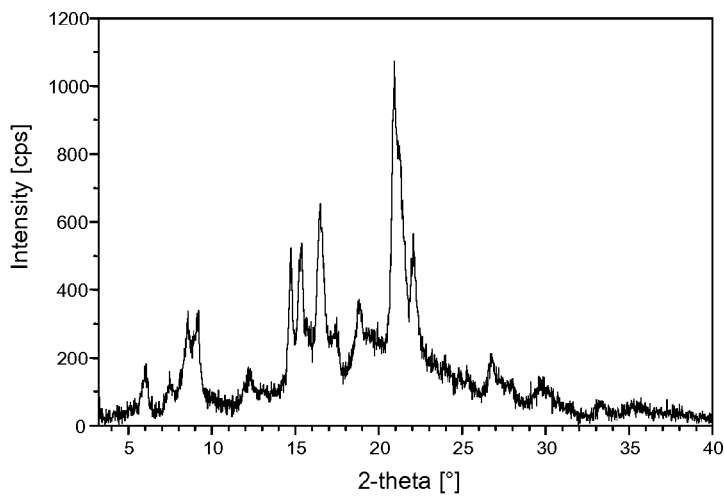

Figure 11a: X-Ray powder diffractogram of the crystalline compound 4-(1,2,4,5-tetrahydro-2-oxo-3*H*-1,3-benzodiazepin-3-yl)-(1*R*)-1-[(4-hydroxy-3,5-dimethylphenyl)methyl]-2-[4-(4-morpholinyl)-1-piperidinyl]-2-oxoethyl 1-piperidinecarboxylate hydrobromide (3a) – polymorph 1.

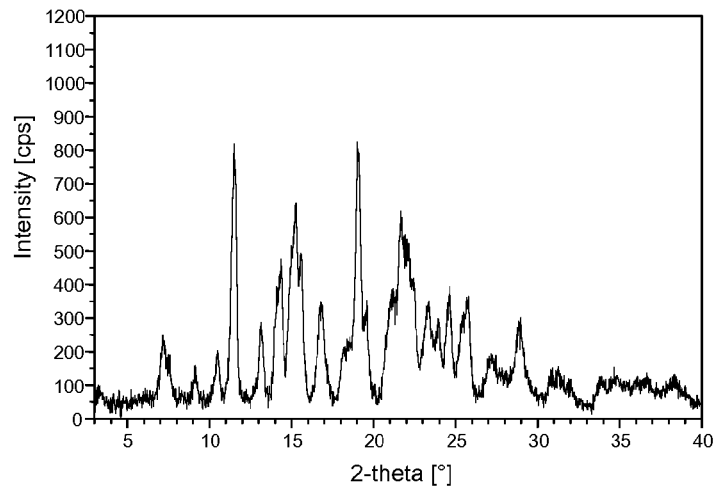

Figure 11b: X-Ray powder diffractogram of the crystalline compound 4-(1,2,4,5-tetrahydro-2-oxo-3*H*-1,3-benzodiazepin-3-yl)-(1*R*)-1-[(4-hydroxy-3,5-dimethylphenyl)methyl]-2-[4-(4-morpholinyl)-1-piperidinyl]-2-oxoethyl 1-piperidinecarboxylate hydrobromide (3a) – polymorph 2.

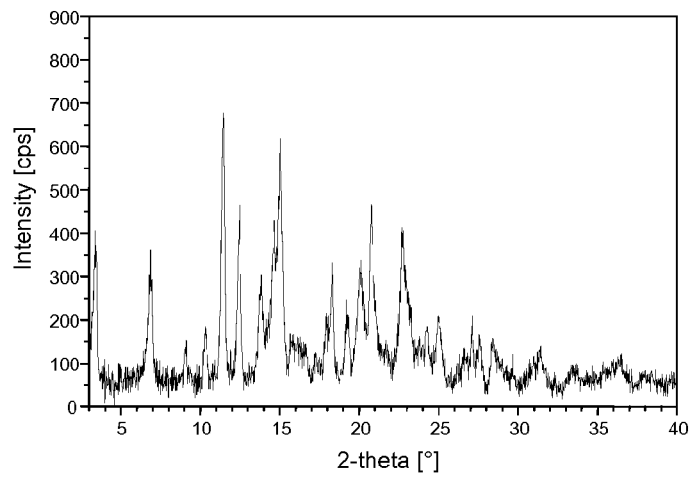

Figure 12a: X-Ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrochloride (3b) – polymorph 1.

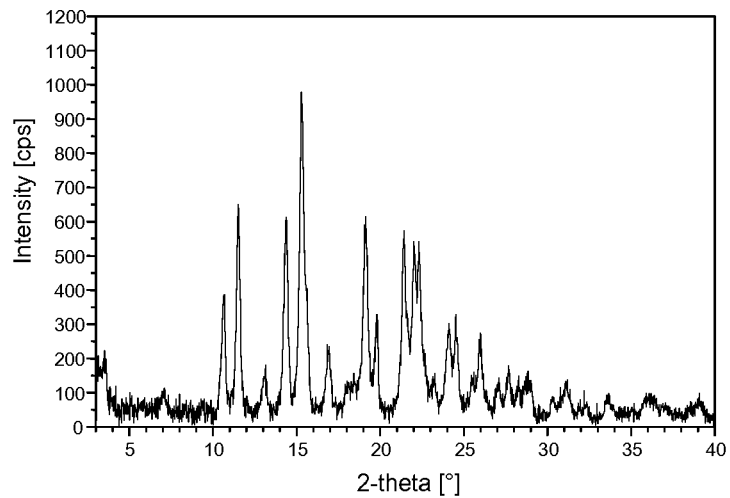

Figure 12b: X-Ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrochloride (3b) – polymorph 2.

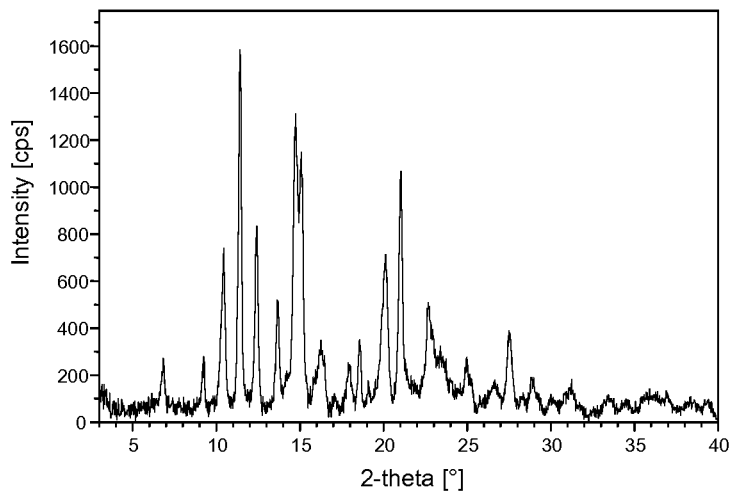

Figure 13: X-Ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate phosphate (3c).

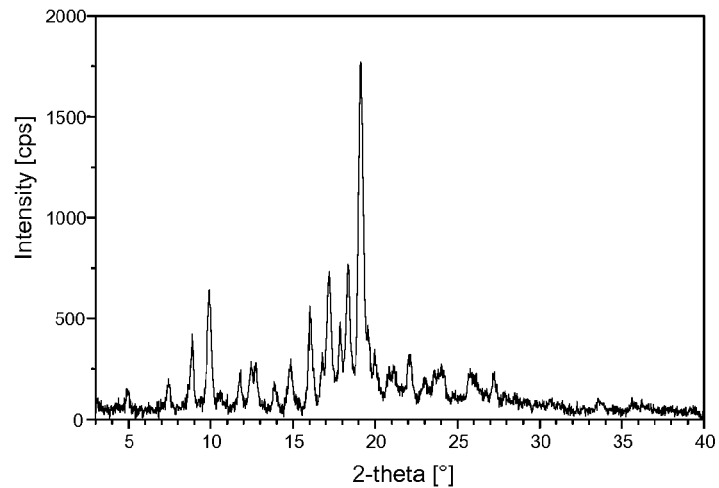

Figure 14: X-Ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2R,3R)-2,3-dihydroxybutanedioate (3d).

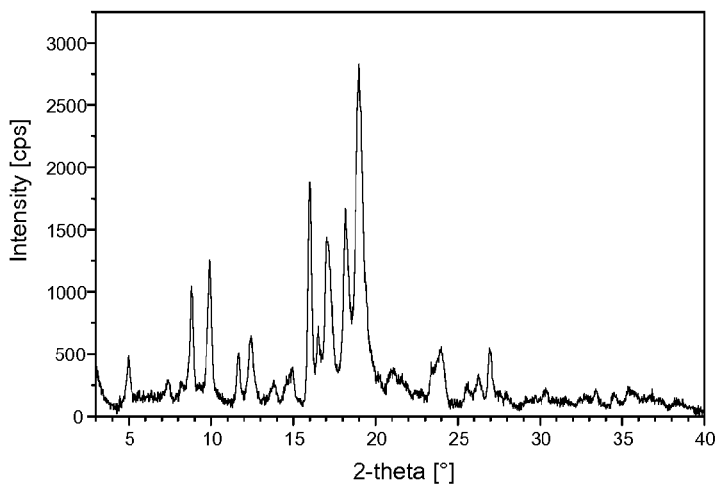

Figure 15: X-Ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2S,3S)-2,3-dihydroxybutanedioate (3e).

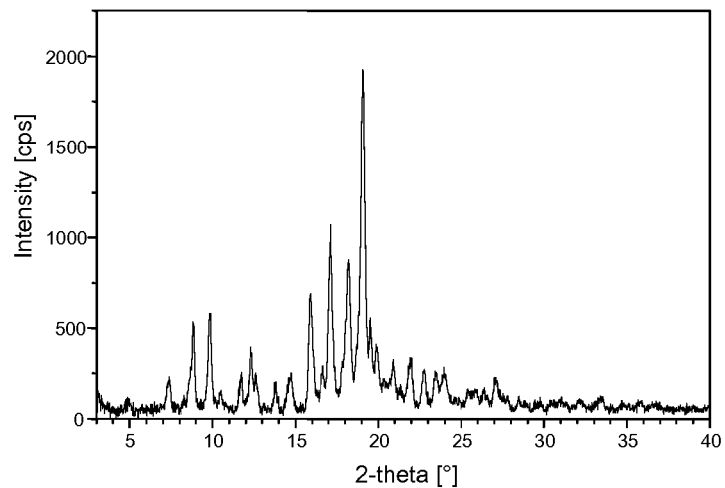

Figure 16: X-Ray powder diffractogram of the crystalline compound (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate fumarate (4a).

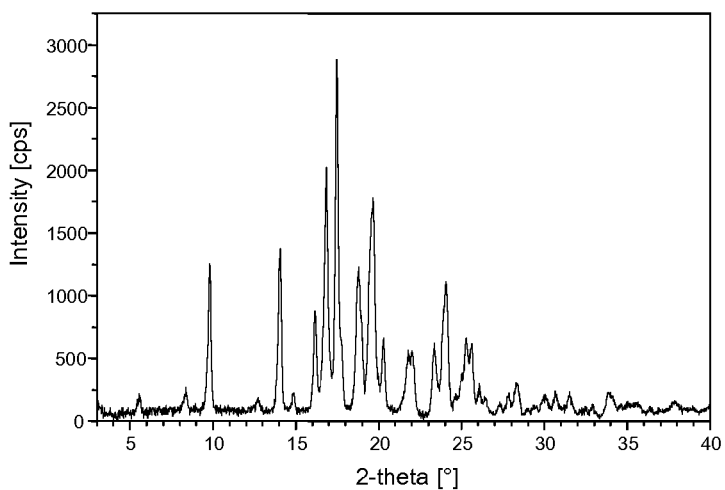

Figure 17: X-Ray powder diffractogram of the crystalline compound (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate sulphate (4b).

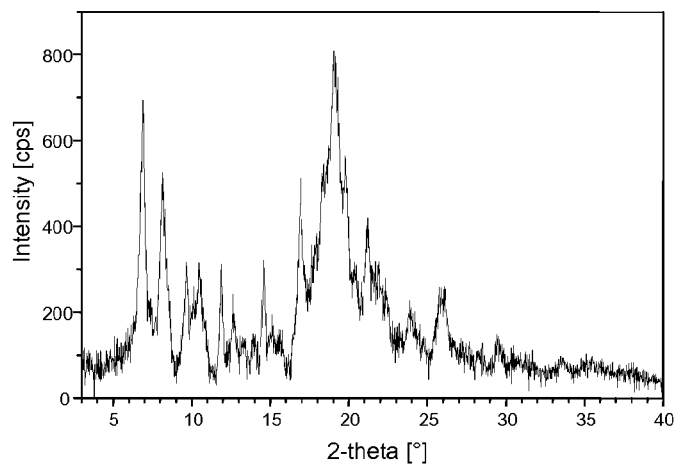

Figure 18: X-Ray powder diffractogram of the crystalline compound (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrochloride-pentahydrate (5a).

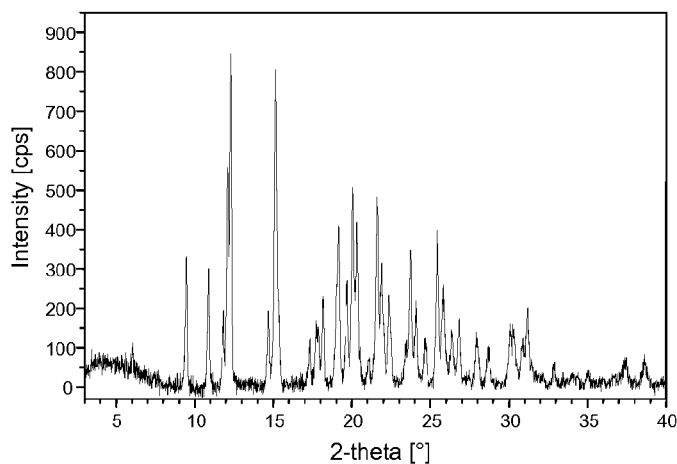

Figure 19: X-Ray powder diffractogram of the crystalline compound (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-(2S,3S)-2,3-dihydroxybutanedioate (5b).

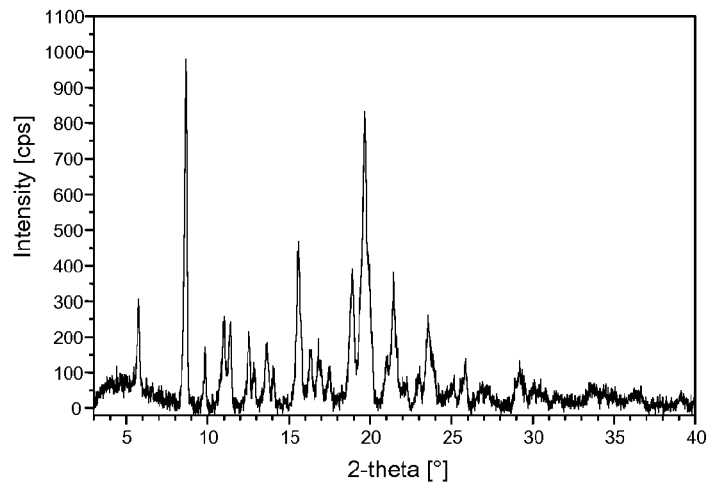

Figure 20: X-Ray powder diffractogram of the crystalline compound (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrobromide-pentahydrate (5c).

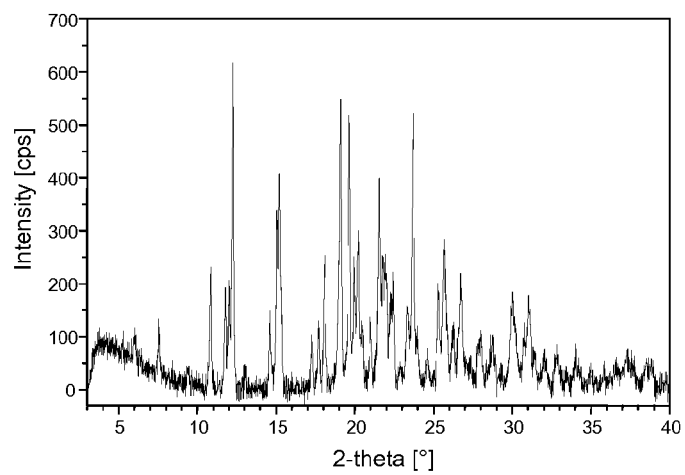

Figure 21: X-Ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-dimaleate (6a).

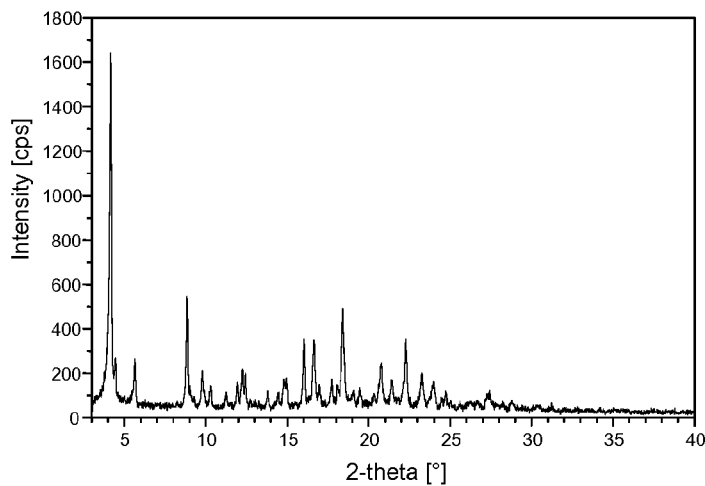

Figure 22: X-Ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-p-toluenesulphonate (6b).

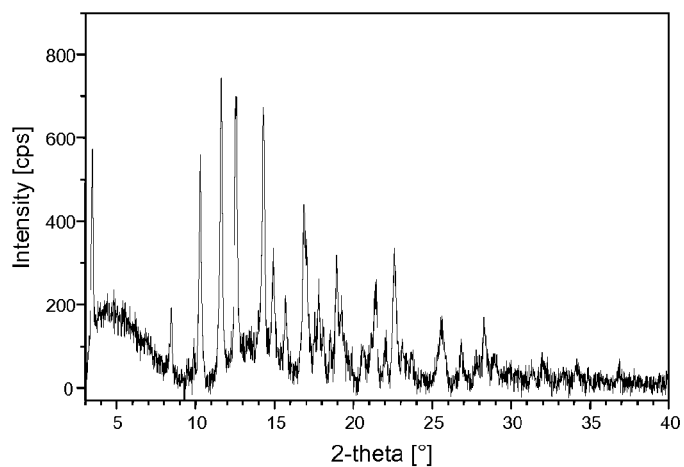

Figure 23: X-Ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-benzenesulphonate (6c).

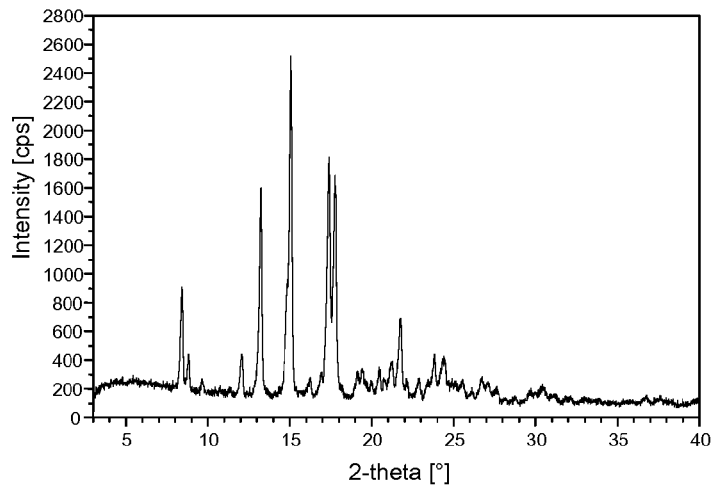

Figure 24: X-Ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-1,5-disulphonate (6d).

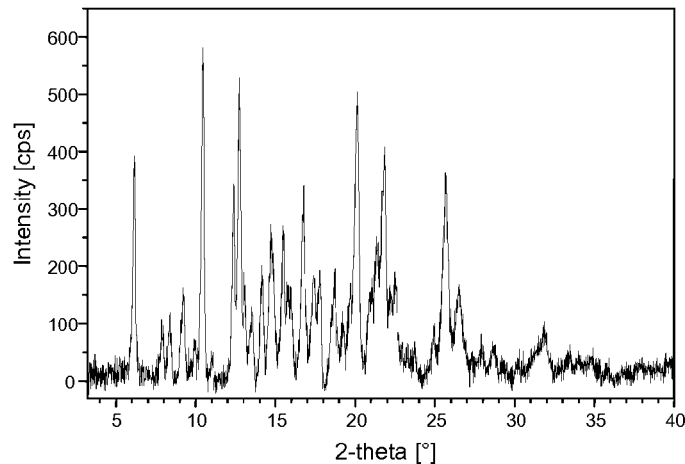

Figure 25: X-Ray powder diffractogram of the crystalline compound 4-(2-oxo-1,2,4,5-tetrahydro-1,3-benzodiazepin-3-yl)-piperidine-1-carboxylic acid-{(*R*)-1-(3,4-diethyl-benzyl)-2-[4-(1-methyl-piperidin-4-yl)-piperazin-1-yl]-2-oxo-ethyl}-amide-naphthalene-2-sulphonate (6e).
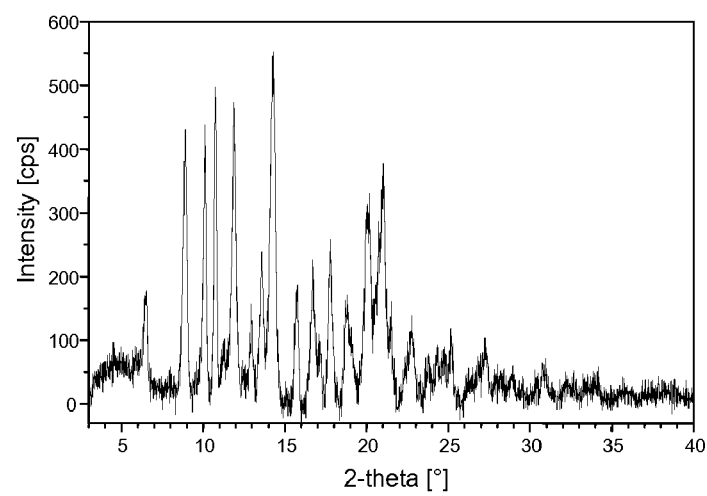

CRYSTALLINE COMPOUNDS

The present invention relates to the new crystalline compounds A of general formula I

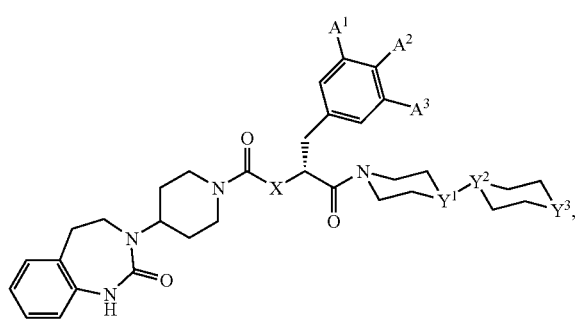

wherein $A^1$, $A^2$, $A^3$, X, $Y^1$, $Y^2$ and $Y^3$ are as defined herein, and which are present in the form of their physiologically acceptable salts with acids, the acids being selected from the group B comprising hydrochloric acid, hydrobromic acid, sulphuric acid, phosphoric acid, benzenesulphonic acid, p-toluenesulphonic acid, maleic acid, succinic acid, fumaric acid, D-(−)-tartaric acid, L-(+)-tartaric acid, naphthalene-2-sulphonic acid and naphthalene-1,5-disulphonic acid, and the polymorphs, the corresponding solvates and hydrates thereof.

BACKGROUND TO THE INVENTION

1. Technical Field

The present invention relates to CGRP-antagonists which are in the form of stable crystalline derivatives and are suitable for the treatment of headaches, particularly for the treatment of migraine.

2. Prior Art

CGRP-antagonists have already been described in International Patent Applications PCT/EP97/04862, PCT/EP03/11762, PCT/EP03/11763 and PCT/EP2005/003094, but not their crystalline forms.

DETAILED DESCRIPTION OF THE INVENTION

The pharmacologically valuable properties of the compounds according to the invention form the basic prerequisite for the effective use of the compound as a pharmaceutical composition. However, an active substance must also comply with other requirements in order to be able to be used as a medicament. These parameters are to a large extent connected with the physicochemical nature of the active substance.

Without being restricted thereto, examples of these parameters are the stability of effect of the starting substance under different ambient conditions, stability in the course of the preparation of the pharmaceutical formulation and stability in the final compositions of the pharmaceutical preparation. The pharmaceutical active substance used to prepare the pharmaceutical compositions should therefore have high stability, which should also be guaranteed even under different environmental conditions. This is absolutely essential to prevent the use of pharmaceutical compositions which contain, in addition to the active substance itself, breakdown products thereof, for example. In such cases the content of active substance found in the pharmaceutical formulations might be less than specified.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. In addition, the uptake of moisture may reduce the content of pharmaceutically active substance during manufacture if the pharmaceutical substance is exposed to the environment without being protected from moisture in any way. Preferably, therefore, a pharmaceutically active substance should be only slightly hygroscopic.

As the crystal modification of an active substance is important to the reproducible active substance content of a preparation, there is a need to clarify as far as possible any existing polymorphism of an active substance present in crystalline form. If there are different polymorphic modifications of an active substance, care must be taken to ensure that the crystalline modification of the substance does not change in the pharmaceutical preparation later produced from it. Otherwise, this could have a harmful effect on the reproducible potency of the drug. Against this background active substances characterised by low polymorphism are preferred.

Another criterion which may be of exceptional importance under certain circumstances depending on the choice of formulation or the choice of manufacturing process for the formulation is the solubility of the active substance. If for example pharmaceutical solutions are prepared (e.g. for infusions), it is essential that the active substance should be sufficiently soluble in physiologically acceptable solvents. It is also very important for drugs which are to be taken orally that the active substance should be sufficiently soluble.

The problem of the present invention is to provide a pharmaceutically active substance which not only is characterised by high pharmacological potency but also satisfies the above-mentioned physicochemical requirements as far as possible.

Surprisingly it has now been found that the problem stated above is solved by the crystalline compounds according to the invention.

In a first aspect the present invention relates to the compounds of the above general formula I wherein $A^1$ denotes Br, —$CH_3$, —$CF_3$ or —$C_2H_5$, $A^2$ denotes —$NH_2$, —OH or —$C_2H_5$, $A^3$ denotes Br, Cl, —$CH_3$ or H, X denotes —$CH_2$, —NH or —O, $Y^1$ denotes N or CH, $Y^2$ denotes N or CH and $Y^3$ denotes —$CH_2$, —N($CH_3$) or —O—, and which are present in the form of their physiologically acceptable salts with acids, the acids being selected from the group B comprising hydrochloric acid, hydrobromic acid, sulphuric acid, phosphoric acid, benzenesulphonic acid, p-toluenesulphonic acid, maleic acid, succinic acid, fumaric acid, D-(−)-tartaric acid, L-(+)-tartaric acid, naphthalene-2-sulphonic acid and naphthalene-1,5-disulphonic acid, and the polymorphs, the corresponding solvates and hydrates thereof.

In a second aspect the present invention relates to the new crystalline CGRP antagonists A of general formula I, which are selected from among

| Number | Structural formula |
|---|---|
| (1) | |
| (2) | |
| (3) | |
| (4) | |

| Number | Structural formula |
|---|---|
| (5) | |
| (6) | | and which are present in the form of their physiologically acceptable salts with acids B which are selected from hydrochloric acid, hydrobromic acid, sulphuric acid, phosphoric acid, benzenesulphonic acid, p-toluenesulphonic acid, maleic acid, succinic acid, fumaric acid, D-(−)-tartaric acid, L-(+)-tartaric acid, naphthalene-2-sulphonic acid and naphthalene-1,5-disulphonic acid as well as the polymorphs, the corresponding solvates and hydrates.

Further aspects of the present invention relate to the following compounds:

(1a) 1-[4-amino-3,5-dibromo-N-[[4-(2,3,4,5-tetrahydro-2 (1H)-oxo-1,3-benzodiazepin-3-yl)-1-piperidinyl]carbonyl]-D-phenylalanyl]-4-(1-piperidinyl)-piperidine-p-toluenesulphonate, (1b) 1-[4-amino-3,5-dibromo-N-[[4-(2,3,4,5-tetrahydro-2 (1H)-oxo-1,3-benzodiazepin-3-yl)-1-piperidinyl]carbonyl]-D-phenylalanyl]-4-(1-piperidinyl)-piperidine-benzenesulphonate, (1c) 1-[4-amino-3,5-dibromo-N-[[4-(2,3,4,5-tetrahydro-2 (1H)-oxo-1,3-benzodiazepin-3-yl)-1-piperidinyl]carbonyl]-D-phenylalanyl]-4-(1-piperidinyl)-piperidine-maleate, (2a) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dimaleate, (2b) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrobromide, (2c) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dihydrobromide, (2d) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrochloride, (2e) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate difumarate, (2f) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate disuccinate, (2g) 4-(2-oxo-1,2,4,5-tetrahydro-1,3-benzodiazepin-3-yl)-piperidine-1-carboxylate (R)-1-(4-amino-3-chloro-5-trifluoromethyl-benzyl)-2-[4-(4-methyl-piperazin-1-yl)-piperidin-1-yl]-2-oxo-ethyl sulphate, (3a) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrobromide, (3b) 4-(1,2,4,5-tetrahydro-2-oxo-3H-1,3-benzodiazepin-3-yl)-(1R)-1-[(4-hydroxy-3,5-dimethylphenyl)methyl]-2-

[4-(4-morpholinyl)-1-piperidinyl]-2-oxoethyl 1-piperidinecarboxylate hydrochloride, (3c) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate phosphate, (3d) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2R,3R)-2,3-dihydroxybutanedioate, (3e) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2S,3S)-2,3-dihydroxybutanedioate, (4a) (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate fumarate, (4b) (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate sulphate, (5a) (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrochloride-pentahydrate, (5b) (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-(2S,3S)-2,3-dihydroxybutanedioate, (5c) (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrobromide-pentahydrate, (6a) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-dimaleate, (6b) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-p-toluenesulphonate, (6c) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-benzenesulphonate, (6d) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-1,5-disulphonate and (6e) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-2-sulphonate, the polymorphs, solvates and hydrates thereof.

The compounds according to the invention are characterised by a high degree of stability and dissolve very easily in physiologically acceptable solvents.

The crystalline salts are in each case characterised by a characteristic melting point, which has been determined by Differential Scanning Calorimetry (DSC: evaluated by means of the onset temperature or peak maximum, heating rate: 10° C./min). The values for the individual compounds listed in Table 1 were determined using a DSC 821 made by Mettler Toledo.

TABLE 1

Melting points of the crystalline salts according to the invention

| Number | melting point $T_{mp.}$ [° C.] |
|---|---|
| (1a) | 180 ± 5 (onset) |
| (1b) | 183 ± 5 (onset) |
| (1c) | 191 ± 5 (onset) |
| (2a) | 200 ± 5 (onset) |
| (2b) | 238 ± 5 (onset) |
| (2c) | 277 ± 5 (onset) |
| (2d) | — |
| (2e) | 218 ± 5 (onset) |
| (2f) | 133 ± 5 (onset) |
| (2g) | 165 ± 5 (peak) |
| (3a) | |
| polymorph 1 | 186 ± 5 (peak) |
| polymorph 2 | 170 ± 5 (peak) |
| (3b) | |
| polymorph 1 | 176 ± 5 (peak) |
| polymorph 2 | 174 ± 5 (peak) |
| (3c) | 209 ± 5 (peak) |
| (3d) | 195 ± 5 (onset) |
| (3e) | 175 ± 5 (onset) |
| (4a) | 222 ± 5 (onset) |
| (4b) | 143 ± 5 (peak) |
| (5a) | 136 ± 5 (peak) |
| (5b) | 144 ± 5 (peak) |
| (5c) | — |
| (6a) | 165 ± 5 (onset) |
| (6b) | 142 ± 5 (peak) |
| (6c) | 199 ± 5 (peak) |
| (6d) | 204 ± 5 (peak) |
| (6e) | 172 ± 5 (peak) |

In another preferred aspect the present invention therefore relates to the crystalline salts according to the invention, in each case characterised by their characteristic melting point.

Another preferred aspect relates to the crystalline compound (1a), characterised by a melting point of $T_{mp.}$=180±5° C.

Another preferred aspect relates to the crystalline compound (1b), characterised by a melting point of $T_{mp.}$=183±5° C.

Another preferred aspect relates to the crystalline compound (1c), characterised by a melting point of $T_{mp.}$=191±5° C.

Another preferred aspect relates to the crystalline compound (2a), characterised by a melting point of $T_{mp.}$=200±5° C.

Another preferred aspect relates to the crystalline compound (2b), characterised by a melting point of $T_{mp.}$=238±5° C.

Another preferred aspect relates to the crystalline compound (2c), characterised by a melting point of $T_{mp.}$=277±5° C.

Another preferred aspect relates to the crystalline compound (2e), characterised by a melting point of $T_{mp.}$=218±5° C.

Another preferred aspect relates to the crystalline compound (2f), characterised by a melting point of $T_{mp.}$=133±5° C.

Another preferred aspect relates to the crystalline compound (2g), characterised by a melting point of $T_{mp.}$=165±5° C.

Another preferred aspect relates to the crystalline compound (3a), polymorph 1), characterised by a melting point of $T_{mp.}$=186±5° C.

Another preferred aspect relates to the crystalline compound (3a), polymorph 2), characterised by a melting point of $T_{mp.}=170\pm5°$ C.

Another preferred aspect relates to the crystalline compound (3b), polymorph 1), characterised by a melting point of $T_{mp.}=176\pm5°$ C.

Another preferred aspect relates to the crystalline compound (3b), polymorph 2), characterised by a melting point of $T_{mp.}=174\pm5°$ C.

Another preferred aspect relates to the crystalline compound (3c), characterised by a melting point of $T_{mp.}=209\pm5°$ C.

Another preferred aspect relates to the crystalline compound (3d), characterised by a melting point of $T_{mp.}=195\pm5°$ C.

Another preferred aspect relates to the crystalline compound (3d), characterised by a water content of between 1.8 and 2.2%.

Another preferred aspect relates to the crystalline compound (3e), characterised by a melting point of $T_{mp.}=175\pm5°$ C.

Another preferred aspect relates to the crystalline compound (4a), characterised by a melting point of $T_{mp.}=222\pm5°$ C.

Another preferred aspect relates to the crystalline compound (4b), characterised by a melting point of $T_{mp.}=143\pm5°$ C.

Another preferred aspect relates to the crystalline compound (5a), characterised by a melting point of $T_{mp.}=136\pm5°$ C.

Another preferred aspect relates to the crystalline compound (5b), characterised by a melting point of $T_{mp.}=144\pm5°$ C.

Another preferred aspect relates to the crystalline compound (6a), characterised by a melting point of $T_{mp.}=165\pm5°$ C.

Another preferred aspect relates to the crystalline compound (6b), characterised by a melting point of $T_{mp.}=142\pm5°$ C.

Another preferred aspect relates to the crystalline compound (6c), characterised by a melting point of $T_{mp.}=199\pm5°$ C.

Another preferred aspect relates to the crystalline compound (6d), characterised by a melting point of $T_{mp.}=204\pm5°$ C.

Another preferred aspect relates to the crystalline compound (6e), characterised by a melting point of $T_{mp.}=172\pm5°$ C.

The crystalline forms of the individual salts according to the invention were investigated more closely by X-ray powder diffraction. The diagrams obtained are shown in FIGS. 1 to 25.

The following Tables 2 to 26 contain a compilation of the data obtained in the analyses carried out.

TABLE 2

X-ray powder reflections and intensities (standardised) of compound (1a).

| d (hkl) [Å] | 2 Θ [°] | intensity I/Io [%] |
|---|---|---|
| 19.49 | 4.53 | 100 |
| 12.16 | 7.26 | 19 |
| 11.06 | 7.99 | 4 |
| 9.71 | 9.1 | 9 |
| 8.17 | 10.82 | 7 |
| 7.36 | 12.02 | 4 |
| 7.09 | 12.48 | 7 |
| 6.91 | 12.79 | 7 |
| 6.46 | 13.69 | 16 |
| 6.08 | 14.56 | 29 |
| 5.4 | 16.39 | 11 |
| 5.17 | 17.13 | 11 |
| 4.84 | 18.31 | 7 |
| 4.56 | 19.44 | 7 |
| 4.5 | 19.73 | 5 |
| 4.39 | 20.22 | 7 |
| 4.3 | 20.64 | 7 |
| 4.13 | 21.5 | 5 |
| 4.04 | 21.96 | 6 |
| 3.92 | 22.64 | 7 |
| 3.82 | 23.26 | 12 |
| 3.77 | 23.57 | 7 |
| 3.66 | 24.28 | 6 |
| 3.5 | 25.4 | 8 |
| 3.44 | 25.85 | 5 |
| 3.34 | 26.69 | 4 |
| 3.23 | 27.58 | 3 |
| 3.17 | 28.12 | 4 |
| 3.06 | 29.14 | 6 |
| 3.05 | 29.3 | 5 |
| 2.92 | 30.55 | 4 |

TABLE 3

X-ray powder reflections and intensities (standardised) of compound (1b).

| d (hkl) [Å] | 2 Θ [°] | intensity I/Io [%] |
|---|---|---|
| 17.6 | 5.02 | 100 |
| 12.29 | 7.18 | 30 |
| 10.22 | 8.65 | 8 |
| 8.77 | 10.08 | 16 |
| 7.82 | 11.31 | 8 |
| 7.24 | 12.22 | 29 |
| 7.08 | 12.48 | 16 |
| 6.64 | 13.33 | 15 |
| 6.14 | 14.43 | 11 |
| 5.84 | 15.16 | 35 |
| 5.73 | 15.45 | 9 |
| 5.34 | 16.58 | 35 |
| 5.25 | 16.87 | 15 |
| 5.06 | 17.5 | 17 |
| 4.88 | 18.16 | 8 |
| 4.7 | 18.85 | 21 |
| 4.53 | 19.59 | 16 |
| 4.38 | 20.26 | 18 |
| 4.16 | 21.36 | 22 |
| 4.08 | 21.76 | 10 |
| 4.02 | 22.12 | 9 |
| 3.96 | 22.42 | 14 |
| 3.91 | 22.71 | 15 |
| 3.84 | 23.17 | 18 |
| 3.78 | 23.49 | 18 |
| 3.68 | 24.18 | 11 |
| 3.62 | 24.55 | 22 |
| 3.43 | 25.92 | 11 |
| 3.4 | 26.18 | 11 |
| 3.32 | 26.83 | 11 |

TABLE 4

X-ray powder reflections and intensities (standardised) of compound (1c).

| d (hkl) [Å] | 2 Θ [°] | intensity I/Io [%] |
|---|---|---|
| 16.14 | 5.47 | 100 |
| 11.7 | 7.55 | 32 |
| 9.88 | 8.94 | 9 |
| 9.58 | 9.22 | 11 |
| 8.52 | 10.38 | 20 |
| 8.12 | 10.89 | 29 |
| 7.82 | 11.3 | 14 |
| 7.61 | 11.62 | 21 |
| 7.04 | 12.56 | 14 |
| 6.3 | 14.06 | 35 |
| 6.15 | 14.39 | 11 |
| 5.82 | 15.2 | 23 |
| 5.71 | 15.49 | 19 |
| 5.61 | 15.79 | 6 |
| 5.4 | 16.39 | 11 |
| 5.31 | 16.7 | 11 |
| 5.24 | 16.91 | 15 |
| 5.04 | 17.58 | 52 |
| 4.94 | 17.93 | 14 |
| 4.75 | 18.65 | 19 |
| 4.61 | 19.25 | 35 |
| 4.55 | 19.51 | 25 |
| 4.43 | 20.04 | 34 |
| 4.27 | 20.78 | 44 |
| 4.07 | 21.79 | 30 |
| 4.03 | 22.06 | 58 |
| 3.8 | 23.36 | 32 |
| 3.66 | 24.3 | 28 |
| 3.47 | 25.64 | 20 |

TABLE 5

X-ray powder reflections and intensities (standardised) of compound (2a).

| d (hkl) [Å] | 2 Θ [°] | intensity I/Io [%] |
|---|---|---|
| 9.97 | 8.86 | 43 |
| 7.92 | 11.16 | 71 |
| 7.62 | 11.61 | 37 |
| 6.99 | 12.66 | 10 |
| 5.65 | 15.67 | 40 |
| 5.57 | 15.9 | 48 |
| 5.45 | 16.25 | 100 |
| 5.33 | 16.6 | 70 |
| 5.29 | 16.75 | 86 |
| 5.17 | 17.15 | 64 |
| 4.99 | 17.77 | 78 |
| 4.83 | 18.35 | 59 |
| 4.66 | 19.05 | 77 |
| 4.59 | 19.31 | 45 |
| 4.45 | 19.92 | 82 |
| 4.27 | 20.78 | 53 |
| 4.1 | 21.63 | 35 |
| 4.02 | 22.07 | 32 |
| 3.96 | 22.44 | 32 |
| 3.82 | 23.25 | 22 |
| 3.65 | 24.39 | 30 |
| 3.6 | 24.7 | 29 |
| 3.48 | 25.61 | 45 |
| 3.41 | 26.09 | 38 |
| 3.32 | 26.85 | 25 |

TABLE 6

X-ray powder reflections and intensities (standardised) of compound (2b).

| d (hkl) [Å] | 2 Θ [°] | intensity I/Io [%] |
|---|---|---|
| 16.83 | 5.25 | 22 |
| 14.75 | 5.99 | 49 |
| 11.14 | 7.93 | 27 |
| 8.48 | 10.42 | 19 |
| 6.74 | 13.13 | 25 |
| 6.42 | 13.79 | 25 |
| 5.9 | 15.02 | 50 |
| 5.67 | 15.61 | 64 |
| 5.57 | 15.9 | 52 |
| 5.28 | 16.76 | 55 |
| 5.14 | 17.25 | 14 |
| 4.84 | 18.3 | 59 |
| 4.71 | 18.82 | 76 |
| 4.49 | 19.74 | 73 |
| 4.39 | 20.21 | 100 |
| 4.21 | 21.09 | 40 |
| 4.08 | 21.75 | 50 |
| 3.97 | 22.36 | 58 |
| 3.9 | 22.78 | 30 |
| 3.77 | 23.56 | 82 |
| 3.71 | 23.95 | 73 |
| 3.6 | 24.73 | 30 |
| 3.45 | 25.82 | 96 |
| 3.09 | 28.87 | 13 |
| 2.99 | 29.84 | 27 |
| 2.9 | 30.77 | 20 |
| 2.83 | 31.55 | 12 |
| 2.75 | 32.55 | 14 |

TABLE 7

X-ray powder reflections and intensities (standardised) of compound (2c).

| d (hkl) [Å] | 2 Θ [°] | intensity I/Io [%] |
|---|---|---|
| 21.69 | 4.07 | 50 |
| 14.51 | 6.08 | 10 |
| 12.67 | 6.97 | 14 |
| 7.69 | 11.5 | 22 |
| 6.78 | 13.04 | 8 |
| 6.28 | 14.1 | 9 |
| 5.81 | 15.23 | 89 |
| 5.57 | 15.91 | 23 |
| 5.37 | 16.5 | 24 |
| 5.25 | 16.89 | 37 |
| 4.98 | 17.81 | 37 |
| 4.74 | 18.7 | 73 |
| 4.63 | 19.16 | 99 |
| 4.51 | 19.65 | 39 |
| 4.42 | 20.08 | 32 |
| 4.3 | 20.66 | 25 |
| 4.15 | 21.42 | 100 |
| 4.05 | 21.92 | 23 |
| 3.9 | 22.81 | 34 |
| 3.84 | 23.12 | 21 |
| 3.78 | 23.51 | 72 |
| 3.57 | 24.9 | 20 |
| 3.51 | 25.33 | 12 |
| 3.43 | 25.98 | 18 |
| 3.36 | 26.49 | 16 |
| 3.25 | 27.44 | 30 |
| 3.19 | 27.98 | 38 |
| 3.03 | 29.49 | 21 |
| 2.95 | 30.23 | 19 |
| 2.9 | 30.84 | 12 |
| 2.86 | 31.3 | 37 |

TABLE 8

X-ray powder reflections and intensities (standardised) of compound (2d).

| d (hkl) [Å] | 2 Θ [°] | intensity I/Io [%] |
|---|---|---|
| 14.06 | 6.28 | 11 |
| 7.59 | 11.65 | 31 |
| 6.7 | 13.21 | 16 |
| 6.16 | 14.37 | 13 |
| 5.78 | 15.31 | 100 |
| 5.59 | 15.83 | 26 |
| 5.36 | 16.53 | 22 |
| 5.21 | 17.01 | 24 |
| 4.95 | 17.91 | 31 |
| 4.69 | 18.89 | 44 |
| 4.59 | 19.31 | 52 |
| 4.12 | 21.55 | 55 |
| 3.86 | 23.01 | 21 |
| 3.73 | 23.82 | 39 |
| 3.4 | 26.18 | 10 |
| 3.17 | 28.15 | 14 |
| 3 | 29.74 | 11 |

TABLE 9

X-ray powder reflections and intensities (standardised) of compound (2e).

| d (hkl) [Å] | 2 Θ [°] | intensity I/Io [%] |
|---|---|---|
| 8.16 | 10.83 | 100 |
| 6.29 | 14.07 | 57 |
| 6.08 | 14.55 | 30 |
| 5.21 | 17.01 | 81 |
| 4.91 | 18.06 | 50 |
| 4.63 | 19.13 | 52 |
| 4.37 | 20.32 | 71 |
| 4.07 | 21.8 | 46 |
| 3.72 | 23.89 | 51 |
| 3.4 | 26.18 | 26 |

TABLE 10

X-ray powder reflections and intensities (standardised) of compound (2f).

| d (hkl) [Å] | 2 Θ [°] | intensity I/Io [%] |
|---|---|---|
| 20.65 | 4.28 | 9 |
| 8.76 | 10.09 | 10 |
| 8.18 | 10.81 | 58 |
| 7.44 | 11.89 | 11 |
| 6.46 | 13.7 | 55 |
| 6.21 | 14.26 | 18 |
| 5.9 | 15 | 12 |
| 5.53 | 16 | 20 |
| 5.39 | 16.44 | 15 |
| 5.26 | 16.83 | 100 |
| 5.18 | 17.11 | 66 |
| 5.01 | 17.7 | 40 |
| 4.61 | 19.23 | 63 |
| 4.46 | 19.89 | 12 |
| 4.32 | 20.53 | 55 |
| 4.09 | 21.7 | 34 |
| 3.9 | 22.8 | 17 |
| 3.75 | 23.71 | 33 |
| 3.66 | 24.31 | 15 |
| 3.57 | 24.9 | 14 |
| 3.41 | 26.12 | 14 |
| 2.77 | 32.3 | 17 |

TABLE 11

X-ray powder reflections and intensities (standardised) of compound (2g).

| d (hkl) [Å] | 2 Θ [°] | intensity I/Io [%] |
|---|---|---|
| 14.81 | 5.96 | 13 |
| 11.81 | 7.48 | 10 |
| 10.27 | 8.6 | 24 |
| 9.67 | 9.14 | 29 |
| 7.25 | 12.21 | 14 |
| 5.98 | 14.81 | 39 |
| 5.78 | 15.33 | 49 |
| 5.37 | 16.5 | 61 |
| 5.1 | 17.36 | 27 |
| 4.72 | 18.77 | 33 |
| 4.24 | 20.94 | 100 |
| 4.02 | 22.07 | 51 |
| 3.34 | 26.69 | 17 |
| 3.01 | 29.61 | 13 |

TABLE 12a

X-ray powder reflections and intensities (standardised) of compound (3a) - polymorph 1

| d (hkl) [Å] | 2 Θ [°] | intensity I/Io [%] |
|---|---|---|
| 12.33 | 7.16 | 29 |
| 9.73 | 9.08 | 11 |
| 8.37 | 10.56 | 18 |
| 7.68 | 11.52 | 97 |
| 6.73 | 13.14 | 32 |
| 6.18 | 14.32 | 56 |
| 5.81 | 15.23 | 73 |
| 5.27 | 16.82 | 41 |
| 4.82 | 18.41 | 28 |
| 4.66 | 19.05 | 100 |
| 4.18 | 21.25 | 46 |
| 4.06 | 21.89 | 55 |
| 3.81 | 23.33 | 40 |
| 3.71 | 23.97 | 35 |
| 3.61 | 24.62 | 42 |
| 3.46 | 25.70 | 41 |
| 3.27 | 27.21 | 18 |
| 3.09 | 28.86 | 34 |
| 2.87 | 31.18 | 9 |

TABLE 12b

X-ray powder reflections and intensities (standardised) of compound (3a) - polymorph 2

| d (hkl) [Å] | 2 Θ [°] | intensity I/Io [%] |
|---|---|---|
| 25.99 | 3.40 | 54 |
| 12.84 | 6.88 | 49 |
| 9.69 | 9.12 | 15 |
| 8.59 | 10.28 | 25 |
| 7.73 | 11.44 | 100 |
| 7.10 | 12.46 | 65 |
| 6.41 | 13.81 | 41 |
| 6.05 | 14.64 | 60 |
| 5.89 | 15.04 | 87 |
| 5.62 | 15.77 | 20 |
| 5.37 | 16.49 | 18 |
| 5.14 | 17.25 | 15 |
| 4.84 | 18.30 | 46 |
| 4.61 | 19.25 | 27 |
| 4.42 | 20.09 | 45 |
| 4.28 | 20.76 | 67 |
| 3.92 | 22.69 | 60 |

TABLE 12b-continued

X-ray powder reflections and intensities (standardised) of compound (3a) - polymorph 2

| d (hkl) [Å] | 2 Θ [°] | intensity I/Io [%] |
|---|---|---|
| 3.67 | 24.25 | 24 |
| 3.56 | 24.97 | 30 |
| 3.29 | 27.05 | 20 |
| 3.23 | 27.57 | 23 |
| 3.13 | 28.49 | 17 |
| 2.84 | 31.46 | 19 |

TABLE 13a

X-ray powder reflections and intensities (standardised) of compound (3b) - polymorph 1.

| d (hkl) [Å] | 2 Θ [°] | intensity I/Io [%] |
|---|---|---|
| 12.47 | 7.08 | 10 |
| 8.31 | 10.64 | 39 |
| 7.68 | 11.51 | 66 |
| 6.78 | 13.05 | 14 |
| 6.15 | 14.38 | 62 |
| 5.79 | 15.29 | 100 |
| 5.25 | 16.88 | 22 |
| 4.91 | 18.03 | 14 |
| 4.81 | 18.43 | 16 |
| 4.64 | 19.13 | 60 |
| 4.48 | 19.79 | 32 |
| 4.15 | 21.42 | 57 |
| 4.03 | 22.02 | 55 |
| 3.83 | 23.19 | 14 |
| 3.69 | 24.11 | 30 |
| 3.63 | 24.52 | 32 |
| 3.49 | 25.54 | 15 |
| 3.42 | 26.00 | 26 |
| 3.30 | 27.04 | 12 |
| 3.21 | 27.68 | 18 |
| 3.16 | 28.22 | 11 |
| 3.10 | 28.81 | 16 |
| 2.95 | 30.29 | 8 |
| 2.88 | 31.06 | 11 |

TABLE 13b

X-ray powder reflections and intensities (standardised) of compound (3b) - polymorph 2.

| d (hkl) [Å] | 2 Θ [°] | intensity I/Io [%] |
|---|---|---|
| 12.92 | 6.83 | 16 |
| 9.56 | 9.25 | 16 |
| 8.48 | 10.43 | 43 |
| 7.74 | 11.42 | 100 |
| 7.13 | 12.40 | 51 |
| 6.48 | 13.66 | 33 |
| 6.00 | 14.74 | 80 |
| 5.88 | 15.06 | 71 |
| 5.45 | 16.25 | 19 |
| 5.20 | 17.05 | 5 |
| 4.93 | 17.97 | 15 |
| 4.78 | 18.57 | 21 |
| 4.65 | 19.08 | 7 |
| 4.41 | 20.10 | 43 |
| 4.22 | 21.03 | 66 |
| 3.92 | 22.67 | 31 |
| 3.79 | 23.45 | 17 |
| 3.56 | 24.98 | 16 |
| 3.34 | 26.65 | 10 |
| 3.24 | 27.52 | 23 |

TABLE 13b-continued

X-ray powder reflections and intensities (standardised) of compound (3b) - polymorph 2.

| d (hkl) [Å] | 2 Θ [°] | intensity I/Io [%] |
|---|---|---|
| 3.15 | 28.29 | 5 |
| 3.08 | 28.93 | 8 |
| 2.97 | 30.05 | 3 |
| 2.86 | 31.22 | 7 |

TABLE 14

X-ray powder reflections and intensities (standardised) of compound (3c).

| d (hkl) [Å] | 2 Θ [°] | intensity I/Io [%] |
|---|---|---|
| 17.96 | 4.92 | 7 |
| 11.81 | 7.48 | 9 |
| 9.96 | 8.87 | 21 |
| 8.90 | 9.93 | 35 |
| 8.35 | 10.58 | 8 |
| 7.51 | 11.78 | 13 |
| 7.09 | 12.47 | 16 |
| 6.92 | 12.77 | 13 |
| 6.38 | 13.87 | 7 |
| 5.95 | 14.88 | 16 |
| 5.53 | 16.03 | 31 |
| 5.27 | 16.80 | 18 |
| 5.15 | 17.20 | 40 |
| 4.96 | 17.87 | 25 |
| 4.83 | 18.34 | 43 |
| 4.63 | 19.14 | 100 |
| 4.44 | 19.99 | 19 |
| 4.27 | 20.81 | 13 |
| 4.20 | 21.16 | 14 |
| 4.02 | 22.09 | 14 |
| 3.86 | 23.05 | 11 |
| 3.76 | 23.67 | 11 |
| 3.70 | 24.06 | 14 |
| 3.45 | 25.79 | 11 |
| 3.28 | 27.18 | 11 |

TABLE 15

X-ray powder reflections and intensities (standardised) of compound (3d).

| d (hkl) [Å] | 2 Θ [°] | intensity I/Io [%] |
|---|---|---|
| 17.77 | 4.97 | 16 |
| 11.87 | 7.44 | 9 |
| 10.66 | 8.29 | 9 |
| 10.02 | 8.81 | 37 |
| 9.53 | 9.27 | 8 |
| 8.90 | 9.93 | 44 |
| 7.59 | 11.65 | 16 |
| 7.11 | 12.43 | 22 |
| 6.41 | 13.80 | 9 |
| 5.93 | 14.94 | 13 |
| 5.54 | 16.00 | 68 |
| 5.36 | 16.51 | 24 |
| 5.20 | 17.04 | 52 |
| 4.88 | 18.17 | 59 |
| 4.67 | 19.00 | 100 |
| 4.23 | 20.97 | 12 |
| 4.09 | 21.69 | 8 |
| 3.80 | 23.39 | 14 |
| 3.71 | 23.98 | 18 |
| 3.48 | 25.61 | 7 |
| 3.39 | 26.25 | 10 |

TABLE 15-continued

X-ray powder reflections and intensities (standardised) of compound (3d).

| d (hkl) [Å] | 2 Θ [°] | intensity I/Io [%] |
|---|---|---|
| 3.31 | 26.94 | 19 |
| 3.20 | 27.89 | 6 |
| 2.94 | 30.41 | 6 |

TABLE 16

X-ray powder reflections and intensities (standardised) of compound (3e).

| d (hkl) [Å] | 2 Θ [°] | intensity I/Io [%] |
|---|---|---|
| 17.99 | 4.91 | 2 |
| 12.00 | 7.36 | 10 |
| 9.97 | 8.86 | 27 |
| 8.97 | 9.86 | 30 |
| 8.41 | 10.51 | 8 |
| 7.54 | 11.72 | 12 |
| 7.18 | 12.31 | 20 |
| 6.99 | 12.65 | 12 |
| 6.73 | 13.14 | 3 |
| 6.41 | 13.81 | 10 |
| 6.01 | 14.73 | 12 |
| 5.57 | 15.90 | 36 |
| 5.33 | 16.62 | 12 |
| 5.17 | 17.12 | 51 |
| 4.87 | 18.21 | 45 |
| 4.65 | 19.07 | 100 |
| 4.55 | 19.51 | 28 |
| 4.46 | 19.89 | 19 |
| 4.36 | 20.36 | 11 |
| 4.24 | 20.94 | 15 |
| 4.16 | 21.35 | 8 |
| 4.04 | 21.96 | 16 |
| 3.90 | 22.76 | 13 |
| 3.79 | 23.44 | 11 |
| 3.71 | 23.96 | 11 |
| 3.50 | 25.41 | 8 |
| 3.44 | 25.88 | 7 |
| 3.38 | 26.33 | 6 |
| 3.29 | 27.08 | 11 |

TABLE 17

X-ray powder reflections and intensities (standardised) of compound (4a).

| d (hkl) [Å] | 2 Θ [°] | intensity I/Io [%] |
|---|---|---|
| 15.80 | 5.59 | 5 |
| 10.53 | 8.39 | 7 |
| 9.01 | 9.81 | 43 |
| 6.95 | 12.72 | 5 |
| 6.30 | 14.05 | 47 |
| 5.97 | 14.83 | 7 |
| 5.48 | 16.15 | 30 |
| 5.26 | 16.85 | 67 |
| 5.07 | 17.49 | 100 |
| 4.72 | 18.78 | 41 |
| 4.52 | 19.61 | 61 |
| 4.38 | 20.27 | 21 |
| 4.07 | 21.81 | 17 |
| 4.04 | 22.01 | 19 |
| 3.81 | 23.35 | 20 |
| 3.70 | 24.04 | 37 |
| 3.52 | 25.30 | 22 |
| 3.47 | 25.66 | 19 |

TABLE 17-continued

X-ray powder reflections and intensities (standardised) of compound (4a).

| d (hkl) [Å] | 2 Θ [°] | intensity I/Io [%] |
|---|---|---|
| 3.42 | 26.02 | 7 |
| 3.37 | 26.45 | 5 |
| 3.27 | 27.26 | 3 |
| 3.15 | 28.27 | 9 |
| 3.08 | 28.94 | 2 |
| 3.03 | 29.43 | 2 |
| 2.98 | 30.01 | 6 |
| 2.91 | 30.6698 | 7 |
| 2.83 | 31.53 | 7 |
| 2.64 | 33.89 | 7 |

TABLE 18

X-ray powder reflections and intensities (standardised) of compound (4b).

| d (hkl) [Å] | 2 Θ [°] | intensity I/Io [%] |
|---|---|---|
| 12.79 | 6.91 | 85 |
| 10.80 | 8.18 | 62 |
| 9.13 | 9.68 | 37 |
| 8.40 | 10.5 | 37 |
| 7.44 | 11.89 | 36 |
| 7.02 | 12.61 | 19 |
| 6.06 | 14.61 | 36 |
| 5.67 | 15.61 | 12 |
| 5.23 | 16.93 | 57 |
| 4.65 | 19.08 | 100 |
| 4.18 | 21.22 | 48 |
| 3.72 | 23.89 | 20 |
| 3.42 | 26.012 | 24 |

TABLE 19

X-ray powder reflections and intensities (standardised) of compound (5a).

| d (hkl) [Å] | 2 Θ [°] | intensity I/Io [%] |
|---|---|---|
| 14.66 | 6.03 | 12 |
| 9.33 | 9.48 | 39 |
| 8.13 | 10.88 | 34 |
| 7.48 | 11.83 | 23 |
| 7.29 | 12.13 | 66 |
| 7.2 | 12.29 | 100 |
| 6.02 | 14.7 | 23 |
| 5.84 | 15.15 | 95 |
| 5.11 | 17.33 | 14 |
| 4.98 | 17.79 | 18 |
| 4.88 | 18.15 | 27 |
| 4.64 | 19.13 | 48 |
| 4.51 | 19.68 | 31 |
| 4.42 | 20.07 | 58 |
| 4.37 | 20.31 | 49 |
| 4.21 | 21.08 | 8 |
| 4.11 | 21.61 | 57 |
| 4.06 | 21.88 | 37 |
| 3.97 | 22.39 | 27 |
| 3.79 | 23.46 | 14 |
| 3.74 | 23.75 | 41 |
| 3.69 | 24.08 | 26 |
| 3.61 | 24.67 | 15 |
| 3.5 | 25.44 | 47 |
| 3.45 | 25.8 | 29 |
| 3.38 | 26.38 | 17 |
| 3.32 | 26.82 | 20 |

TABLE 19-continued

X-ray powder reflections and intensities (standardised) of compound (5a).

| d (hkl) [Å] | 2 Θ [°] | intensity I/Io [%] |
|---|---|---|
| 3.19 | 27.96 | 15 |
| 3.11 | 28.68 | 12 |
| 2.97 | 30.07 | 19 |
| 2.95 | 30.31 | 17 |
| 2.9 | 30.85 | 14 |
| 2.87 | 31.17 | 24 |

TABLE 20

X-ray powder reflections and intensities (standardised) of compound (5b).

| d (hkl) [Å] | 2 Θ [°] | intensity I/Io [%] |
|---|---|---|
| 15.37 | 5.74 | 30 |
| 10.21 | 8.66 | 100 |
| 8.98 | 9.84 | 16 |
| 8.05 | 10.98 | 26 |
| 7.77 | 11.38 | 24 |
| 7.06 | 12.52 | 20 |
| 6.87 | 12.88 | 12 |
| 6.49 | 13.63 | 19 |
| 6.3 | 14.05 | 12 |
| 5.99 | 14.77 | 2 |
| 5.67 | 15.61 | 48 |
| 5.43 | 16.31 | 17 |
| 5.25 | 16.87 | 14 |
| 5.07 | 17.47 | 12 |
| 4.7 | 18.88 | 40 |
| 4.51 | 19.66 | 85 |
| 4.43 | 20.03 | 29 |
| 4.22 | 21.04 | 15 |
| 4.14 | 21.44 | 39 |
| 4.01 | 22.14 | 7 |
| 3.86 | 23 | 9 |
| 3.77 | 23.6 | 24 |
| 3.55 | 25.1 | 7 |
| 3.45 | 25.82 | 13 |
| 3.32 | 26.84 | 7 |
| 3.27 | 27.23 | 7 |
| 3.05 | 29.22 | 14 |
| 2.97 | 30.05 | 7 |

TABLE 21

X-ray powder reflections and intensities (standardised) of compound (5c).

| d (hkl) [Å] | 2 Θ [°] | intensity I/Io [%] |
|---|---|---|
| 14.65 | 6.03 | 19 |
| 11.71 | 7.55 | 22 |
| 9.42 | 9.38 | 7 |
| 8.17 | 10.82 | 35 |
| 7.5 | 11.78 | 31 |
| 7.22 | 12.24 | 100 |
| 6.8 | 13.00 | 8 |
| 6.05 | 14.62 | 24 |
| 5.83 | 15.19 | 67 |
| 5.13 | 17.26 | 17 |
| 5.01 | 17.69 | 21 |
| 4.9 | 18.07 | 38 |
| 4.65 | 19.08 | 85 |
| 4.52 | 19.64 | 84 |
| 4.45 | 19.95 | 41 |
| 4.39 | 20.20 | 42 |

TABLE 21-continued

X-ray powder reflections and intensities (standardised) of compound (5c).

| d (hkl) [Å] | 2 Θ [°] | intensity I/Io [%] |
|---|---|---|
| 4.23 | 21.00 | 22 |
| 4.12 | 21.56 | 65 |
| 4.06 | 21.87 | 34 |
| 3.99 | 22.27 | 31 |
| 3.81 | 23.36 | 25 |
| 3.75 | 23.69 | 77 |
| 3.61 | 24.62 | 13 |
| 3.51 | 25.32 | 32 |
| 3.46 | 25.69 | 46 |
| 3.39 | 26.23 | 20 |
| 3.33 | 26.74 | 36 |
| 3.19 | 27.99 | 21 |
| 3.11 | 28.73 | 17 |
| 2.98 | 30.01 | 30 |
| 2.88 | 31.06 | 24 |
| 2.79 | 32.02 | 13 |
| 2.73 | 32.82 | 14 |

TABLE 22

X-ray powder reflections and intensities (standardised) of compound (6a).

| d (hkl) [Å] | 2 Θ [°] | intensity I/Io [%] |
|---|---|---|
| 21.21 | 4.16 | 100 |
| 19.91 | 4.43 | 16 |
| 15.64 | 5.64 | 16 |
| 9.99 | 8.85 | 33 |
| 9.58 | 9.22 | 5 |
| 9.02 | 9.8 | 13 |
| 8.59 | 10.29 | 9 |
| 7.85 | 11.26 | 7 |
| 7.41 | 11.94 | 10 |
| 7.23 | 12.23 | 13 |
| 7.12 | 12.42 | 12 |
| 6.79 | 13.03 | 5 |
| 6.41 | 13.8 | 7 |
| 6.13 | 14.45 | 7 |
| 5.94 | 14.9 | 10 |
| 5.7 | 15.54 | 4 |
| 5.52 | 16.04 | 20 |
| 5.33 | 16.62 | 21 |
| 5.22 | 16.98 | 9 |
| 5.12 | 17.31 | 5 |
| 5 | 17.73 | 11 |
| 4.9 | 18.08 | 9 |
| 4.81 | 18.42 | 30 |
| 4.65 | 19.06 | 8 |
| 4.56 | 19.46 | 7 |
| 4.36 | 20.33 | 7 |
| 4.28 | 20.76 | 15 |
| 4.14 | 21.43 | 10 |
| 3.99 | 22.27 | 22 |
| 3.82 | 23.26 | 12 |
| 3.71 | 23.96 | 10 |
| 3.63 | 24.51 | 5 |
| 3.6 | 24.73 | 7 |
| 3.56 | 25.01 | 5 |

TABLE 23

X-ray powder reflections and intensities (standardised) of compound (6b).

| d (hkl) [Å] | 2 Θ [°] | intensity I/Io [%] |
|---|---|---|
| 25.57 | 3.45 | 70 |
| 10.46 | 8.44 | 26 |
| 9.26 | 9.54 | 10 |
| 8.93 | 9.9 | 16 |
| 8.59 | 10.29 | 75 |
| 7.61 | 11.61 | 100 |
| 7.04 | 12.57 | 94 |
| 6.19 | 14.3 | 91 |
| 5.93 | 14.92 | 45 |
| 5.64 | 15.71 | 30 |
| 5.25 | 16.88 | 57 |
| 4.98 | 17.79 | 35 |
| 4.91 | 18.06 | 22 |
| 4.78 | 18.55 | 19 |
| 4.68 | 18.95 | 43 |
| 4.61 | 19.24 | 30 |
| 4.48 | 19.8 | 7 |
| 4.31 | 20.61 | 14 |
| 4.15 | 21.4 | 33 |
| 4.03 | 22.05 | 9 |
| 3.93 | 22.6 | 45 |
| 3.84 | 23.13 | 16 |
| 3.75 | 23.72 | 10 |
| 3.65 | 24.38 | 4 |
| 3.48 | 25.59 | 23 |
| 3.32 | 26.83 | 16 |

TABLE 24

X-ray powder reflections and intensities (standardised) of compound (6c).

| d (hkl) [Å] | 2 Θ [°] | intensity I/Io [%] |
|---|---|---|
| 10.53 | 8.40 | 36 |
| 10.04 | 8.80 | 18 |
| 9.16 | 9.65 | 11 |
| 7.78 | 11.36 | 8 |
| 7.33 | 12.06 | 18 |
| 6.68 | 13.24 | 63 |
| 5.99 | 14.79 | 30 |
| 5.87 | 15.08 | 100 |
| 5.56 | 16.21 | 11 |
| 5.23 | 16.94 | 13 |
| 5.10 | 17.39 | 72 |
| 5.00 | 17.76 | 67 |
| 4.88 | 18.15 | 9 |
| 4.63 | 19.15 | 13 |
| 4.56 | 19.43 | 14 |
| 4.44 | 19.98 | 10 |
| 4.33 | 20.48 | 14 |
| 4.72 | 20.79 | 11 |
| 4.18 | 21.21 | 15 |
| 4.08 | 21.74 | 28 |
| 4.01 | 22.14 | 11 |
| 3.99 | 22.87 | 11 |
| 3.79 | 23.43 | 11 |
| 3.73 | 23.81 | 15 |
| 3.04 | 24.41 | 17 |

TABLE 25

X-ray powder reflections and intensities (standardised) of compound (6d).

| d (hkl) [Å] | 2 Θ [°] | intensity I/Io [%] |
|---|---|---|
| 14.35 | 6.15 | 71 |
| 12.71 | 6.95 | 4 |
| 11.2 | 7.89 | 20 |
| 10.55 | 8.38 | 22 |
| 9.59 | 9.22 | 30 |
| 8.89 | 9.95 | 11 |
| 8.47 | 10.43 | 100 |
| 8.03 | 11.01 | 7 |
| 7.15 | 12.37 | 62 |
| 6.95 | 12.73 | 96 |
| 6.76 | 13.09 | 30 |
| 6.55 | 13.52 | 24 |
| 6.25 | 14.15 | 36 |
| 6.01 | 14.73 | 50 |
| 5.72 | 15.48 | 49 |
| 5.57 | 15.91 | 25 |
| 5.29 | 16.73 | 58 |
| 5.09 | 17.41 | 33 |
| 4.99 | 17.77 | 34 |
| 4.74 | 18.69 | 35 |
| 4.61 | 19.24 | 22 |
| 4.51 | 19.68 | 28 |
| 4.41 | 20.12 | 91 |
| 4.23 | 20.98 | 28 |
| 4.16 | 21.36 | 46 |
| 4.07 | 21.81 | 71 |
| 3.95 | 22.5 | 33 |
| 3.75 | 23.73 | 12 |
| 3.57 | 24.94 | 17 |
| 3.47 | 25.68 | 60 |
| 3.36 | 26.51 | 30 |
| 3.2 | 27.9 | 15 |
| 3.11 | 28.67 | 11 |
| 3.05 | 29.22 | 6 |

TABLE 26

X-ray powder reflections and intensities (standardised) of compound (6e).

| d (hkl) [Å] | 2 Θ [°] | intensity I/Io [%] |
|---|---|---|
| 13.63 | 6.48 | 33 |
| 9.93 | 8.9 | 83 |
| 8.75 | 10.1 | 84 |
| 8.22 | 10.76 | 96 |
| 7.87 | 11.24 | 18 |
| 7.43 | 11.9 | 91 |
| 6.82 | 12.97 | 25 |
| 6.52 | 13.57 | 46 |
| 6.21 | 14.26 | 100 |
| 5.86 | 15.1 | 3 |
| 5.63 | 15.73 | 35 |
| 5.3 | 16.73 | 41 |
| 5.17 | 17.14 | 19 |
| 4.99 | 17.75 | 50 |
| 4.72 | 18.78 | 33 |
| 4.65 | 19.08 | 19 |
| 4.42 | 20.07 | 61 |
| 4.23 | 21.01 | 73 |
| 4.13 | 21.48 | 26 |
| 3.98 | 22.34 | 9 |
| 3.91 | 22.74 | 25 |
| 3.74 | 23.79 | 15 |
| 3.66 | 24.32 | 17 |
| 3.6 | 24.74 | 17 |
| 3.54 | 25.17 | 23 |

In the above Tables 2 to 26 the value "2Θ[°]" denotes the diffraction angle in degrees and the value "d (hkl) [Å]" denotes the intervals in Å measured between the lattice planes.

The X-ray powder diagrams of the compounds (1a), (1b), (1c), (5a), (5b), (5c), (6a), (6b), (6c), (6d) and (6e) were recorded within the scope of the present invention using a BRUKER D8 Advanced System in bragg-brentano geometry, equipped with a site-sensitive detector (SSD) and a Cu anode as the X-ray source with filtered CuK$_\alpha$ radiation (λ=1.5418 Å, 40 kV, 40 mA).

The X-ray powder diagrams of the compounds (2a), (2b), (2c), (2d), (2e), (2f), (2g), (3a), (3b), (3c), (3d), (3e), (4a) and (4b) were recorded within the scope of the present invention using a STOE-STADI P diffractometer in transmission mode, equipped with a site-sensitive detector (SSD) and a Cu anode as X-ray source with monochromatic CuK$_\alpha$ radiation (λ=1.54056 Å, 40 kV, 40 mA).

According to the findings shown in Table 2 the present invention relates to crystalline 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]4-(1-piperidinyl)-piperidine-p-toluenesulphonate (1a), characterised in that in the X-ray powder diagram it has, inter alia, the characteristic values d=19.49 Å, 12.16 Å, 6.46 Å, 6.08 Å, 5.4 Å, 5.17 Å and 3.82 Å.

According to the findings shown in Table 3 the present invention relates to crystalline 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]4-(1-piperidinyl)-piperidine-benzenesulphonate (1b), characterised in that in the X-ray powder diagram it has, inter alia, the characteristic values d=17.6 Å, 12.29 Å, 7.24 Å, 5.84 Å and 5.34 Å.

According to the findings shown in Table 4 the present invention relates to crystalline 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]4-(1-piperidinyl)-piperidine-maleate (1c), characterised in that in the X-ray powder diagram it has, inter alia, the characteristic values d=16.14 Å, 11.7 Å, 6.3 Å, 5.04 Å, 4.61 Å, 4.43 Å, 4.03 Å and 3.8 Å.

According to the findings shown in Table 5 the present invention relates to crystalline (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dimaleate (2a), characterised in that in the X-ray powder diagram it has, inter alia, the characteristic values d=7.92 Å, 5.45 Å, 5.29 Å, 4.99 Å, 4.66 Å and 4.45 Å.

According to the findings shown in Table 6 the present invention relates to crystalline (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrobromide (2b), characterised in that in the X-ray powder diagram it has, inter alia, the characteristic values d=4.71 Å, 4.49 Å, 4.39 Å, 3.77 Å, 3.71 Å and 3.45 Å.

According to the findings shown in Table 7 the present invention relates to crystalline (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dihydrobromide (2c), characterised in that in the X-ray powder diagram it has, inter alia, the characteristic values d=21.69 Å, 5.81 Å, 4.74 Å, 4.63 Å, 4.15 Å and 3.78 Å.

According to the findings shown in Table 8 the present invention relates to crystalline (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrochloride (2d), characterised in that in the X-ray powder diagram it has, inter alia, the characteristic values d=7.59 Å, 5.78 Å, 4.95 Å, 4.69 Å, 4.59 Å, 4.12 Å and 3.73 Å.

According to the findings shown in Table 9 the present invention relates to crystalline (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate difumarate (2e), characterised in that in the X-ray powder diagram it has, inter alia, the characteristic values d=8.16 Å, 6.29 Å, 5.21 Å, 4.63 Å, 4.37 Å and 3.72 Å.

According to the findings shown in Table 10 the present invention relates to crystalline (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate disuccinate (2f), characterised in that in the X-ray powder diagram it has, inter alia, the characteristic values d=8.18 Å, 6.46 Å, 5.26 Å, 5.18 Å, 4.61 Å and 4.32 Å.

According to the findings shown in Table 11 the present invention relates to crystalline (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate sulphate (2g), characterised in that in the X-ray powder diagram it has, inter alia, the characteristic values d=5.98 Å, 5.78 Å, 5.37 Å, 4.24 Å and 4.02 Å.

According to the findings shown in Table 12a the present invention relates to crystalline 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxo ethyl 1-piperidinecarboxylate hydrobromide (3a, polymorph 1), characterised in that in the X-ray powder diagram it has, inter alia, the characteristic values d=7.86 Å, 6.18 Å, 5.81 Å, 4.66 Å and 4.06 Å.

According to the findings shown in Table 12b the present invention relates to crystalline 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxo ethyl 1-piperidinecarboxylate hydrobromide (3a, polymorph 2), characterised in that in the X-ray powder diagram it has, inter alia, the characteristic values d=25.99 Å, 7.73 Å, 7.10 Å, 6.05 Å, 5.89 Å, 4.28 Å and 3.92 Å.

According to the findings shown in Table 13a the present invention relates to crystalline 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxo ethyl 1-piperidinecarboxylate hydrochloride (3b, polymorph 1), characterised in that in the X-ray powder diagram it has, inter alia, the characteristic values d=7.68 Å, 6.15 Å, 5.79 Å, 4.64 Å, 4.15 Å and 4.03 Å.

According to the findings shown in Table 13b the present invention relates to crystalline 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxo ethyl 1-piperidinecarboxylate hydrochloride (3b, polymorph 2), characterised in that in the X-ray powder diagram it has, inter alia, the characteristic values d=7.74 Å, 7.13 Å, 6.00 Å, 5.88 Å and 4.22 Å.

According to the findings shown in Table 14 the present invention relates to crystalline 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxo ethyl 1-piperidinecarboxylate phosphate (3c), characterised in that in the X-ray powder diagram it has, inter alia, the characteristic values d=8.90 Å, 5.53 Å, 5.15 Å, 4.83 Å and 4.63 Å.

According to the findings shown in Table 15 the present invention relates to crystalline 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2R,3R)-2,3-dihydroxybutanedioate (3d), characterised in that in the X-ray powder diagram it has, inter alia, the characteristic values d=10.02 Å, 8.90 Å, 5.54 Å, 5.20 Å, 4.88 Å and 4.67 Å.

According to the findings shown in Table 16 the present invention relates to crystalline 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxo ethyl 1-piperidinecarboxylate (2S,3S)-2,3-dihydroxybutanedioate (3e), characterised in that in the X-ray powder diagram it has, inter alia, the characteristic values d=8.97 Å, 5.57 Å, 5.17 Å, 4.87 Å and 4.65 Å.

According to the findings shown in Table 17 the present invention relates to crystalline (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate fumarate (4a), characterised in that in the X-ray powder diagram it has, inter alia, the characteristic values d=9.01 Å, 6.30 Å, 5.26 Å, 5.07 Å, 4.72 Å and 4.52 Å.

According to the findings shown in Table 18 the present invention relates to crystalline (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate sulphate (4b), characterised in that in the X-ray powder diagram it has, inter alia, the characteristic values d=12.79 Å, 10.80 Å, 5.23 Å, 4.65 Å and 4.18 Å.

According to the findings shown in Table 19 the present invention relates to crystalline (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrochloride-pentahydrate (5a), characterised in that in the X-ray powder diagram it has, inter alia, the characteristic values d=7.29 Å, 7.2 Å, 5.84 Å, 4.42 Å and 4.11 Å.

According to the findings shown in Table 20 the present invention relates to crystalline (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-(2S,3S)-2,3-dihydroxybutanedioate (5b), characterised in that in the X-ray powder diagram it has, inter alia, the characteristic values d=10.21 Å, 5.67 Å, 4.7 Å, 4.51 Å and 4.14 Å.

According to the findings shown in Table 21 the present invention relates to crystalline (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrobromide-pentahydrate (5c), characterised in that in the X-ray powder diagram it has, inter alia, the characteristic values d=7.22 Å, 5.83 Å, 4.65 Å, 4.52 Å, 4.12 Å and 3.75 Å.

According to the findings shown in Table 22 the present invention relates to crystalline 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-dimaleate (6a), characterised in that in the X-ray powder diagram it has, inter alia, the characteristic values d=21.21 Å, 9.99 Å, 5.52 Å, 5.33 Å, 4.81 Å and 3.99 Å.

According to the findings shown in Table 23 the present invention relates to crystalline 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-p-toluenesulphonate (6b), characterised in that in the X-ray powder diagram it has, inter alia, the characteristic values d=25.57 Å, 8.59 Å, 7.61 Å, 7.04 Å, 6.19 Å and 5.25 Å.

According to the findings shown in Table 24 the present invention relates to crystalline 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-benzenesulphonate (6c), characterised in that in the X-ray powder diagram it has, inter alia, the characteristic values d=10.53 Å, 6.68 Å, 5.87 Å, 5.10 Å and 5.00 Å.

According to the findings shown in Table 25 the present invention relates to crystalline 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-1,5-disulphonate (6d), characterised in that in the X-ray powder diagram it has, inter alia, the characteristic values d=8.47 Å, 7.15 Å, 6.95 Å, 5.29 Å, 4.41 Å, 4.07 Å and 3.47 Å.

According to the findings shown in Table 26 the present invention relates to crystalline 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-2-sulphonate (6e), characterised in that in the X-ray powder diagram it has, inter alia, the characteristic values d=9.93 Å, 8.75 Å, 8.22 Å, 7.43 Å, 6.21 Å, 4.42 Å and 4.23 Å.

Methods of Preparation

As an example of a preferred method of preparation according to the present invention the preparation of the crystalline salt 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2R,3R)-2,3-dihydroxybutanedioate (3d) according to the invention will be described in more detail, comprising the following steps:

(a) mixing the base 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxyate with a first solvent at ambient temperature and subsequently heating the suspension formed;

(b) adding a second solvent and subsequently heating the reaction mixture;

(c) dropwise addition of a concentrated solution of (L)-(+)-tartaric acid in water;

(d) slow cooling of the reaction mixture, filtering and drying the crystals formed.

The preparation of the compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate of formula II

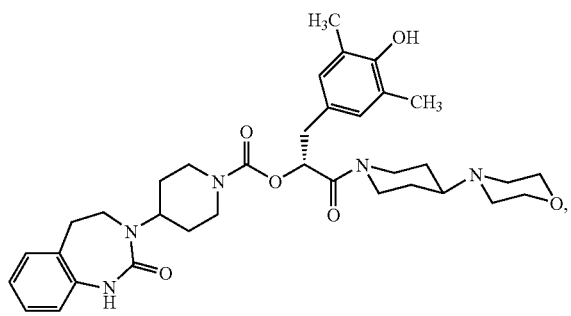

(II)

used as starting material is described in International Patent Application PCT/EP2005/003094.

The solvent used in step (a) may be according to the invention methanol, ethanol, propanol, isopropanol or a mixture of these solvents, while ethanol or isopropanol or a 1:1 mixture of ethanol and isopropanol is preferred according to the invention.

The solvent in step (a) is used in an amount of from 2 to 5 mL/mmol of the base used, preferably in an amount of from 3 to 4 mL/mmol of base used.

The suspension formed in step (a) is then heated to a temperature of 50 to 60° C.

The solvent used in step (b) according to the invention may be methanol, ethanol, propanol, isopropanol or a mixture of these solvents, while ethanol or isopropanol or a 1:1 mixture of ethanol and isopropanol is preferred according to the invention.

The solvent in step (b) is used in an amount of from 2 to 5 mL/mmol of base used, preferably in an amount of from 3 to 4 mL/mmol of base used.

The reaction mixture obtained in step (b) is then heated to a temperature of 70 to 80° C., preferably to a temperature of 74 to 76° C.

It is particularly preferred according to the invention to use ethanol as the solvent in step (a) and isopropanol as the solvent in step (b).

The solvent used in step (c) is a quantity of water equivalent to the amount of tartaric acid used. The water is used in an amount of 0.9 to 1.1 g/g of tartaric acid used, preferably in an amount of 1.0 g/g of tartaric acid used.

It is also preferred according to the invention to use 0.9 eq to 1.1 eq, preferably 1.0 eq of the acid used in step (c), in each case based on the amount of base used.

To accelerate the crystallisation process the solution obtained in step (c) may be inoculated with the desired form of the tartrate (3d).

Corresponding methods of preparing each of the salts mentioned previously are described in the following experimental section.

The preparation methods described are also suitable for use on an industrial scale for preparing large quantities of substance.

In a third aspect the present invention relates to the use of the crystalline salts as pharmaceutical compositions in view of their pharmaceutical efficacy.

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, preferably irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the present use of the CGRP antagonists in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for treating irritable bowel syndrome (IBS) and for the preventive and acute-therapeutic treatment of hot flushes in oestrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, one to three times a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiinflammatories, corticosteroids, calcium antagonists, 5-HT$_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other 5-HT$_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. mGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. iNOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. sst2 receptor agonists may be added.

The dosage of these active substances is expediently 1/5 of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more of the compounds according to the invention.

It is particularly preferable if the compounds of formula I are administered orally, and it is particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds according to the invention are administered by inhalation, particularly preferably if they are administered once or twice a day. For this purpose, the compounds according to the invention have to be made available in forms suitable for inhalation. Inhalable preparations include inhalable powders, propellant-containing metered-dose aerosols or propellant-free inhalable solutions, which are optionally present in admixture with conventional physiologically acceptable excipients.

EXPERIMENTAL SECTION

The compounds of general formula I may be prepared using methods known in principle. The methods listed in the "*Handbook of Pharmaceutical Salts*" (Eds. P. Heinrich Stahl, Camille G. Wermuth, Wiley-VHC 2002) have proved particularly suitable.

Example 1

1-[4-amino-3,5-dibromo-N-[[4-(2,3,4,5-tetrahydro-2 (1H)-oxo-1,3-benzodiazepin-3-yl)-1-piperidinyl] carbonyl]-D-phenylalanyl]-4-(1-piperidinyl)-piperi- dine-p-toluenesulphonate (1a)

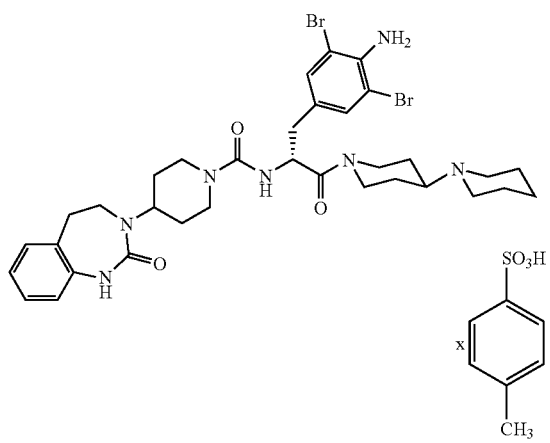

1.52 g (2.0 mmol) 1-[4-amino-3,5-dibromo-N-[[4-(2,3,4, 5-tetrahydro-2(1H)-oxo-1,3-benzodiazepin-3-yl)-1-piperidinyl]carbonyl]-(D)-phenylalanyl]-4-(-1-piperidinyl)-piperidine are suspended in 20 ml of ethanol at 50° C. and 380 mg (2.0 mmol) p-toluene-sulphonic acid monohydrate are added batchwise. The mixture is heated to 65° C., during which time a clear solution is formed. On cooling to 50° C. a white precipitate is produced. The suspension is stirred for 12 hours at ambient temperature and filtered. The solid is washed with 3 ml of ethanol and dried for 12 hours at 45° C.

Yield: 1.41 g (76% of theory)

Example 2

1-[4-amino-3,5-dibromo-N-[[4-(2,3,4,5-tetrahydro-2 (1H)-oxo-1,3-benzodiazepin-3-yl)-1-piperidinyl] carbonyl]-D-phenylalanyl]-4-(1-piperidinyl)-piperi- dine-benzenesulphonate (1b)

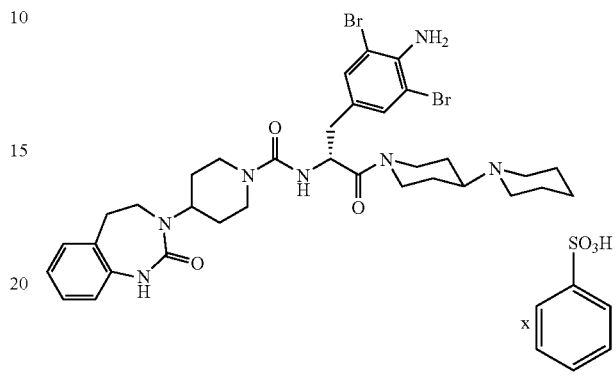

7.6 g (10.0 mmol) 1-[4-amino-3,5-dibromo-N-[[4-(2,3,4, 5-tetrahydro-2(1H)-oxo-1,3-benzodiazepin-3-yl)-1-piperidinyl]carbonyl]-(D)-phenylalanyl]-4-(-1-piperidinyl)-piperidine are suspended in 100 ml of ethanol at 50° C. and 1.6 g (10.0 mmol) benzene-sulphonic acid are added batchwise. After the addition of 0.18 ml of water the mixture is cooled to 45° C. and stirred for 8 hours at this temperature. Then the mixture is stirred for 7 days at 40° C., during which time a precipitate is formed. Then the suspension formed is stirred for 7 days at 35° C., 7 days at 30° C. and 3 days at ambient temperature. The solid formed is filtered off, washed with 15 ml of ethanol and dried for 12 hours at 45° C.

Yield: 5.08 g (55% of theory)

Example 3

1-[4-amino-3,5-dibromo-N-[[4-(2,3,4,5-tetrahydro-2 (1H)-oxo-1,3-benzodiazepin-3-yl)-1-piperidinyl] carbonyl]-D-phenylalanyl]-4-(1-piperidinyl)-piperi- dine-maleate (1c)

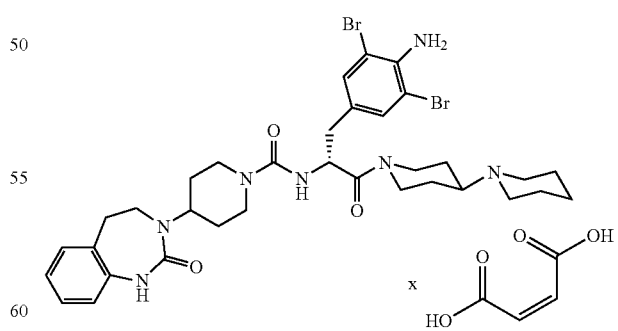

1.52 g (2.0 mmol) 1-[4-amino-3,5-dibromo-N-[[4-(2,3,4, 5-tetrahydro-2(1H)-oxo-1,3-benzodiazepin-3-yl)-1-piperidinyl]carbonyl]-(D)-phenylalanyl]-4-(-1-piperidinyl)-piperidine are suspended in 20 ml of ethanol at 60° C. and 0.23 g (2.0 mmol) maleic acid are added batchwise. The mixture is cooled to ambient temperature and stirred for 3 days. The solid formed is filtered off, washed with 3 ml of ethanol and dried for 12 hours at 45° C.

Yield: 0.82 g (47% of theory)

Example 4

(R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dimaleate (2a)

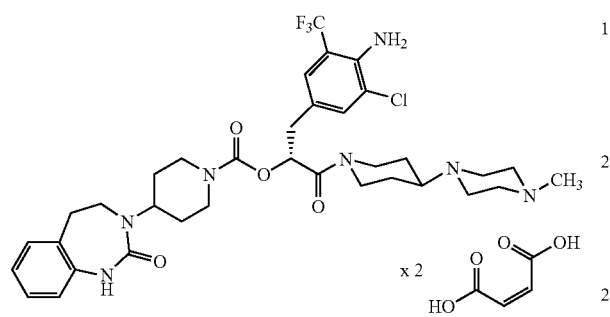

1.0 g (1.39 mmol) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate are dissolved in 10 ml of ethanol at ambient temperature and combined with 322 mg (2.78 mmol) maleic acid. The mixture is heated to 70° C., during which time a white precipitate is formed. The suspension is cooled to ambient temperature over 8 hours and filtered at 5° C. The isolated crystals are dried for 12 hours at 50° C.

Yield: 1.08 g (82% of theory)

Example 5

(R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrobromide (2b)

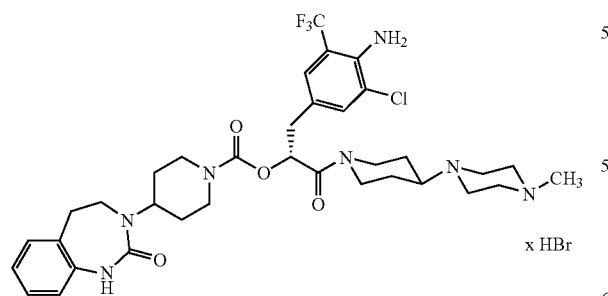

0.5 g (0.69 mmol) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate are dissolved in 5 ml of ethanol at ambient temperature and combined with 78 µl hydrobromic acid (48% in water). The mixture is heated to 70° C., whereupon a light yellow solution is formed. This solution is stirred for 3 days at 50° C., during which time a white precipitate is formed. After cooling to ambient temperature the solid formed is filtered off and dried for 12 hours at 40° C.

Yield: 70 mg (13% of theory)

Example 6

(R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dihydrobromide (2c)

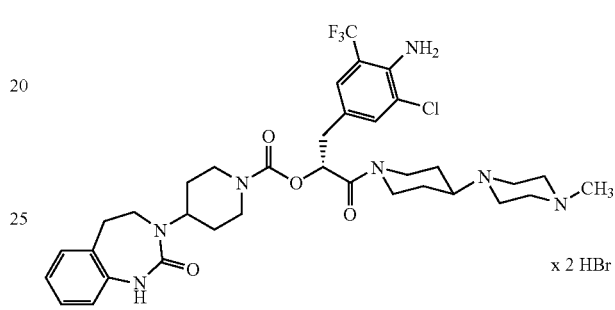

0.5 g of (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate (chemical purity: 85%, 0.59 mmol) are dissolved in 5 ml of ethanol at ambient temperature and combined with 235 µl hydrobromic acid (30% in glacial acetic acid), whereupon a white precipitate is immediately formed. The suspension is stirred for 5 hours at ambient temperature, diluted with a little ethanol and filtered. The isolated solid is dried for 12 hours at 70° C.

Yield: 480 mg (92% of theory)

Example 7

(R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrochloride (2d)

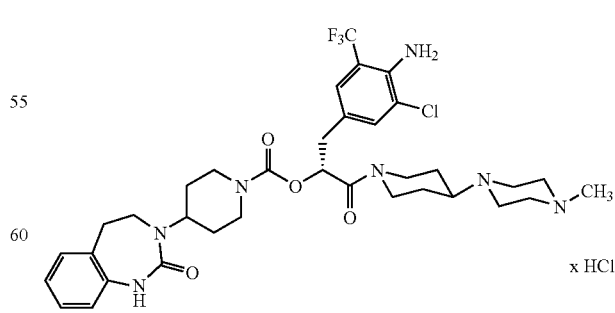

0.5 g (0.69 mmol) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate are dissolved in 5 ml isopropanol at ambient temperature. After the addition of 95.2 μl hydrochloric acid (12.4 mol/l in ethanol) a white precipitate is formed spontaneously. After 12 hours at ambient temperature the precipitate formed is filtered off and dried at 70° C.

Yield: 0.19 g (41% of theory)

Example 8

(R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate difumarate (2e)

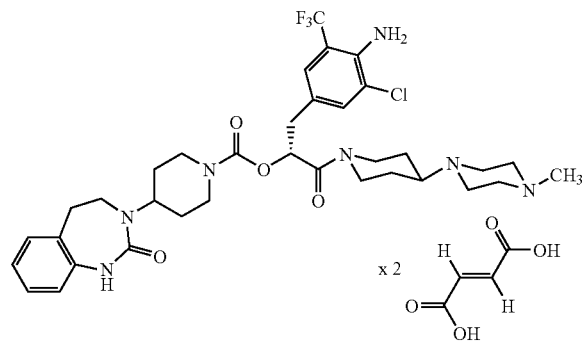

2.5 g (2.95 mmol) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate are dissolved in 25 ml of ethanol at ambient temperature, combined with 685 mg (5.9 mmol) fumaric acid and heated to 45° C. A viscous suspension is formed, which is diluted by the addition of 15 ml of ethanol. The mixture is heated to 70° C., during which time a white precipitate is formed. The suspension formed is diluted with another 5 ml of ethanol, cooled to 26° C. and filtered. The isolated solid is dried for 12 hours at 60° C.

Yield: 2.49 g (89% of theory)

Example 9

(R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate disuccinate (2f)

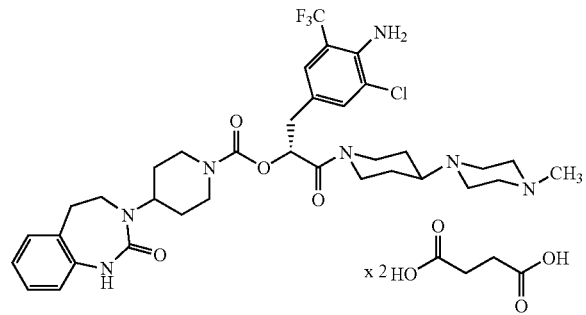

0.5 g (0.69 mmol) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate are dissolved in 5 ml isopropanol at ambient temperature, combined with 82 mg (0.69 mmol) succinic acid and heated to 50° C. After 18 hours at 50° C. a white precipitate has formed. The suspension is cooled to 30° C., filtered, washed with isopropanol and dried.

Yield: 0.24 g (36% of theory)

Example 10

(R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate sulphate (2g)

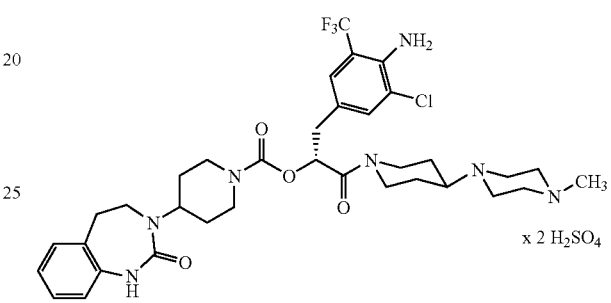

0.5 g (0.69 mmol) (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate are dissolved in 10 ml of methanol at ambient temperature. After the addition of 100 μl sulphuric acid (48% in water) the mixture is stirred for 3 hours at ambient temperature. After about 5 ml of methanol has been evaporated off, 1 ml of tert-butylmethylether is added, whereupon an oil is precipitated. After removal of the supernatant solvent the residue is combined with 5 ml acetone, during which time crystallisation sets in. The precipitate formed is filtered and dried for 12 hours at 30° C.

Yield: 0.26 g (46% of theory)

Example 11

4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrobromide (3a)

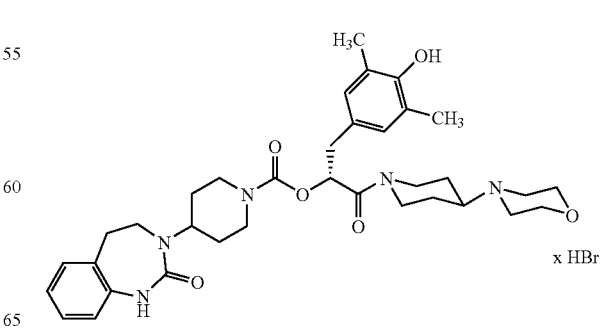

(11a) Polymorph 1; Form B 0.5 g (0.79 mmol) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate are suspended in 5 ml acetone at ambient temperature. The suspension formed is heated to 52° C. and combined with 1.0 ml of ethanol, during which time a clear solution is formed. After the addition of 157 µl hydrobromic acid (30% in glacial acetic acid) the solution is cooled to ambient temperature over 5 hours. The solution is combined with 2.5 ml n-butyl acetate, whereupon turbidity sets in. The suspension formed is heated to 60° C. for 20 minutes, then cooled to 45° C. and stirred for 12 hours at this temperature. After cooling to ambient temperature the precipitate formed is filtered off, washed with acetone and dried for 6 hours at 80° C.

Yield: 520 mg (92% of theory)

(11b) Polymorph 2; Form A 0.5 g (0.79 mmol) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate are suspended in 5 ml n-propanol at ambient temperature and heated to 70° C. After the addition of 157 µl hydrobromic acid (30% in glacial acetic acid) the mixture is stirred for 1 hour at 70° C. and 20 hours at 40° C. Then the suspension formed is cooled to ambient temperature, stirred for 5 hours and filtered. The residue is dried for 4 hours at 80° C.

Yield: 460 mg (72% of theory)

Example 12

4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrochloride (3b)

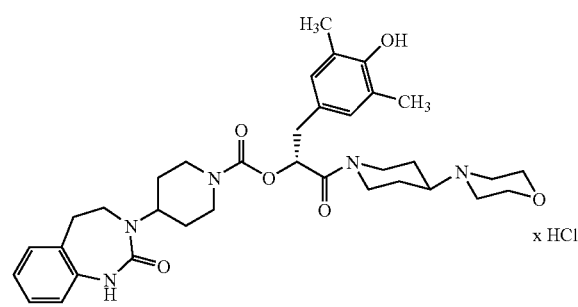

(12a) Polymorph 1; Form B 0.5 g (0.79 mmol) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate are dissolved in 5 ml isopropanol at 70° C. and combined with 69.2 µl hydrochloric acid (11.4 mol/l in ethanol), whereupon turbidity sets in. After 1.5 hours at 70° C. 3 ml isopropanol are added to dilute the suspension formed. The mixture is cooled stepwise to ambient temperature within 2.5 hours, filtered and dried for 12 hours at 55° C. To eliminate the solvent completely the solid is dried for a further 6 hours at 65° C. and for 5 hours at 80° C.

Yield: 470 mg (84% of theory)

(12b) Polymorph 2; Form A 0.5 g (0.79 mmol) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate are dissolved in 5 ml of ethanol at ambient temperature and combined with 65.3 µl hydrochloric acid (37% in water). After 2 hours at ambient temperature tert-butylmethylether is added dropwise until turbidity sets in. After another 2 hours at ambient temperature the white precipitate formed is filtered off, washed with tert-butyl-methylether and dried for 12 hours at 40° C.

Yield: 370 mg (70% of theory)

Example 13

4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate phosphate (3c)

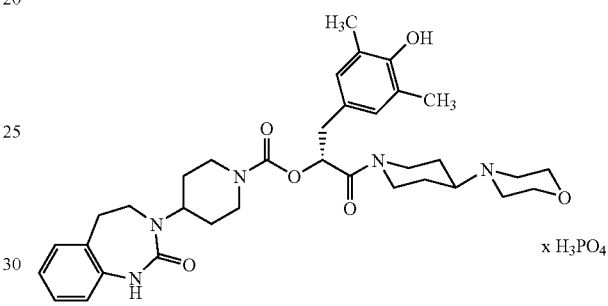

1.0 g (1.58 mmol) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate are dissolved in 8.9 ml boiling ethanol and combined with a solution of 106 µl phosphoric acid (85% in water) in 1.06 ml of ethanol. The mixture is stirred for 2 hours at 72° C., whereupon a white suspension is formed. After cooling the suspension is stirred for 12 hours at ambient temperature. The crystals formed are filtered off and dried for 12 hours at 40° C.

Yield: 520 mg (44% of theory)

Example 14

4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2R,3R)-2,3-dihydroxybutanedioate (3d)

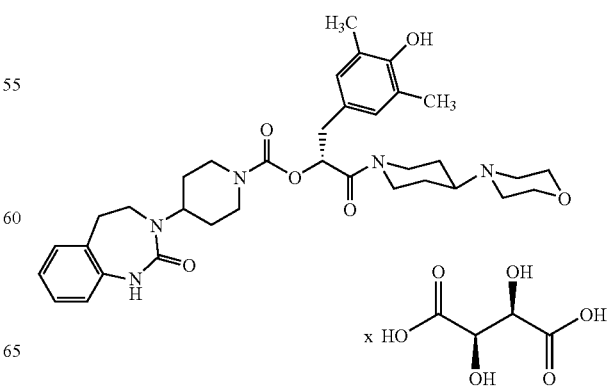

39.4 g (57.8 mmol, 93%)) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate are taken up in 197 ml of ethanol at ambient temperature. The mixture is heated to 70° C., while 197 ml isopropanol are added. At 75° C. a solution of 10.25 g (67.6 mmol) (L)-(+)-tartaric acid in 10.25 ml of water is added dropwise. After inoculation with the desired polymorph the mixture is cooled to 18° C. within 4 hours. The crystals formed are filtered off, washed with ethanol and dried.

Yield: 38.8 g (84% of theory)

Example 15

4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2S,3S)-2,3-dihydroxybutanedioate (3e)

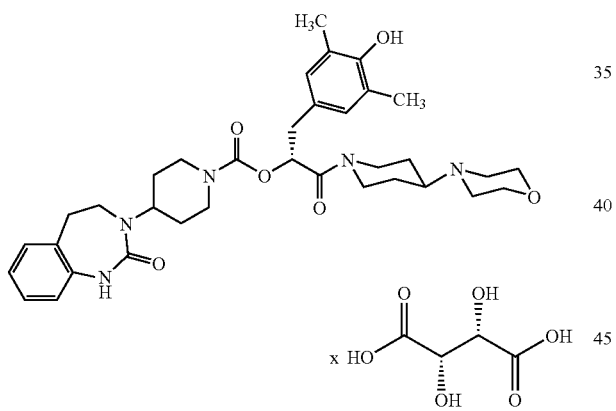

2.0 g (3.16 mmol) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate are dissolved in 15 ml boiling isopropanol. 479 mg (3.16 mmol) (D)-(−)-tartaric acid are dissolved in 5 ml boiling isopropanol and while still hot added dropwise to the isopropanolic solution of the base. The mixture is refluxed for 1.5 hours until a white suspension has formed. After cooling the suspension is stirred for 1 hour at ambient temperature. The crystals formed are filtered off and dried for 12 hours at 40° C.

Yield: 2.1 g (81% of theory)

Example 16

(R)-1-(4-hydroxy-3,5-dimethyl-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate fumarate (4a)

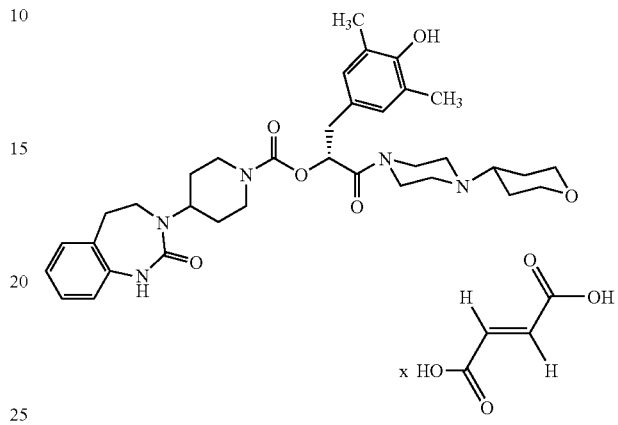

0.25 g (0.39 mmol) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-tetrahydropyranyl)-1-piperazinyl]-2-oxoethyl 1-piperidinecarboxylate and 46.7 mg (0.39 mmol) fumaric acid are dissolved in 2.5 ml of ethanol and 4 drops of water at 70° C. The mixture is cooled to ambient temperature over 12 hours, during which time a colourless suspension is formed. The crystals formed are filtered off, washed with ethanol and dried for 12 hours at 40° C.

Yield: 170 mg (57% of theory)

Example 17

(R)-1-(4-hydroxy-3,5-dimethyl-benzyl)-2-oxo-2-[4-(tetrahydro-pyran-4-yl)-piperazin-1-yl]-ethyl 4-(2-oxo-1,2,4,5-tetrahydro-1,3-benzodiazepin-3-yl)-piperidine-1-carboxylate sulphate (4b)

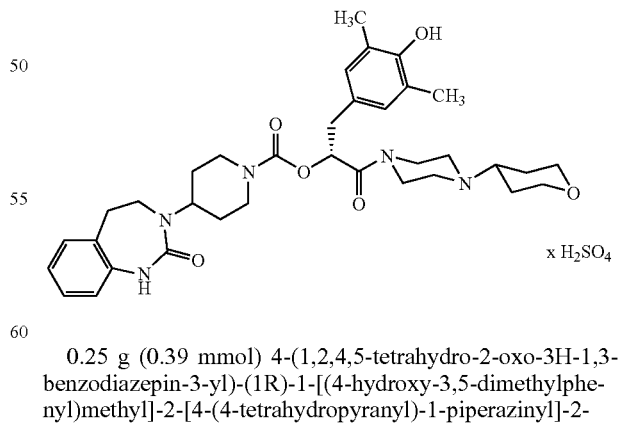

0.25 g (0.39 mmol) 4-(1,2,4,5-tetrahydro-2-oxo-3H-1,3-benzodiazepin-3-yl)-(1R)-1-[(4-hydroxy-3,5-dimethylphenyl)methyl]-2-[4-(4-tetrahydropyranyl)-1-piperazinyl]-2-oxoethyl 1-piperidinecarboxylate are dissolved in 1.75 ml isopropanol and heated to 70° C. 22.2 μL sulphuric acid (95% in water) are added at this temperature, whereupon a colourless precipitate is formed. The suspension formed is cooled to ambient temperature within 2.5 hours. The crystals formed are filtered off, washed with isopropanol washed and dried for 12 hours at 45° C.

Yield: 260 mg (90% of theory)

Example 18

(S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrochloride pentahydrate (5a)

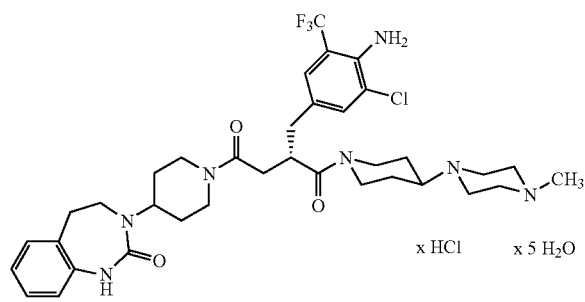

3.0 g (4.2 mmol) (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione are dissolved in 3 ml acetone and combined with a solution of 4.2 ml hydrochloric acid (1 mol/l in water) in 22.8 ml of water. The mixture is refluxed and cooled to ambient temperature within 12 hours. The solid formed is filtered off and dried for 12 hours at 40° C.

Yield: 3.0 g (85% of theory)

Example 19

(S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-(2S,3S)-2,3-dihydroxybutanedioate (5b)

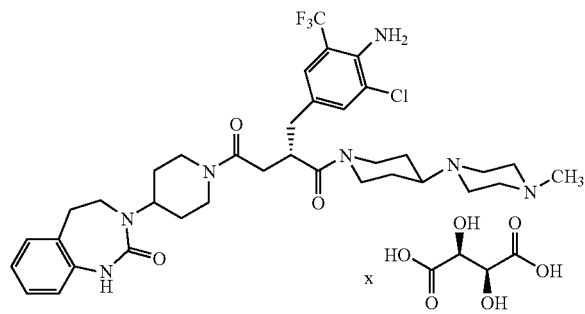

0.5 g (0.7 mmol) (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione and 209 mg (1.4 mmol) (D)-(−)-tartaric acid are dissolved in 5 ml of water and refluxed. Then the solution is cooled to ambient temperature within 12 hours. The solid formed is filtered off and dried for 12 hours at 40° C.

Yield: 0.5 g (71% of theory)

Example 20

(S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrobromide-pentahydrate (5c)

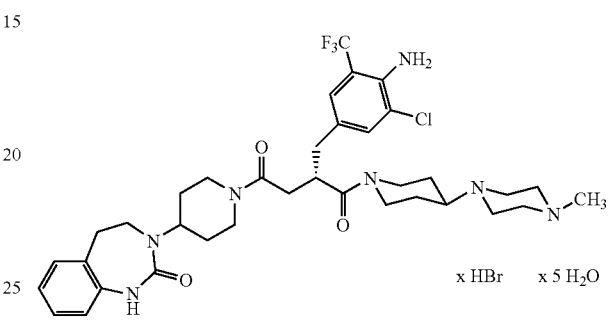

2.0 g (2.6 mmol) (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione are dissolved in 20 ml isopropanol and at 50° C. combined with 0.6 ml hydrobromic acid (47% in water). The mixture is cooled to 4° C. within 30 minutes. The solid formed is filtered off, washed with 5 ml cold isopropanol and dried for 12 hours at 40° C.

Yield: 1.94 g (83% of theory)

Example 21

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-dimaleate (6a)

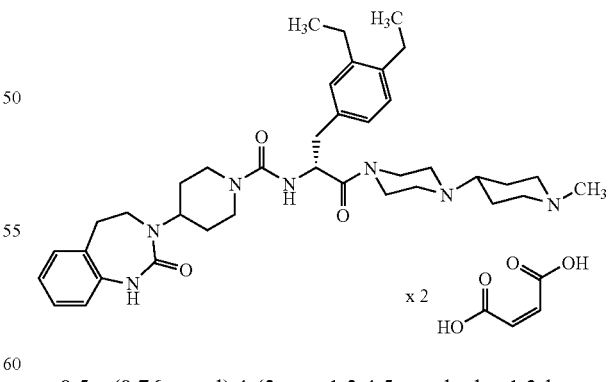

0.5 g (0.76 mmol) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide and 88 mg (0.76 mmol) maleic acid are suspended in 10 ml acetone and refluxed. 1 ml of methanol is added to this suspension, whereupon the substances go into solution completely. After the addition of another 5 ml acetone the solution is stirred for 2 days at ambient temperature. The solid formed on the glass wall is dissolved and another 10 ml acetone are added. The precipitate formed is filtered off and dried for 12 hours at 40° C.

Yield: 20 mg (3% of theory)

Example 22

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-p-toluenesulphonate (6b)

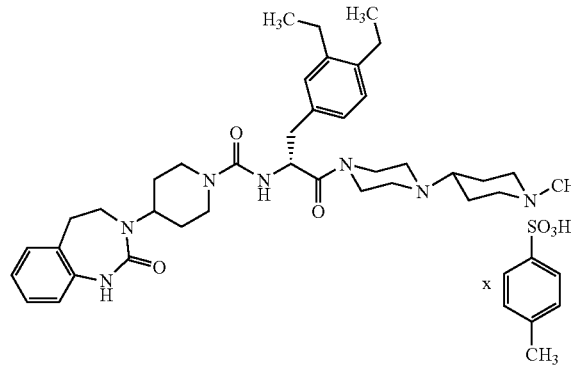

0.2 g (0.30 mmol) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide and 57.8 mg (0.30 mmol) p-toluenesulphonic acid are suspended in 10 ml acetone and refluxed. 1 ml of methanol is added to this suspension, whereupon the substance goes into solution completely. After cooling to ambient temperature the solid formed is filtered off, washed with acetone and dried for 12 hours at 40° C.

Yield: 120 mg (47% of theory)

Example 23

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-benzenesulphonate (6c)

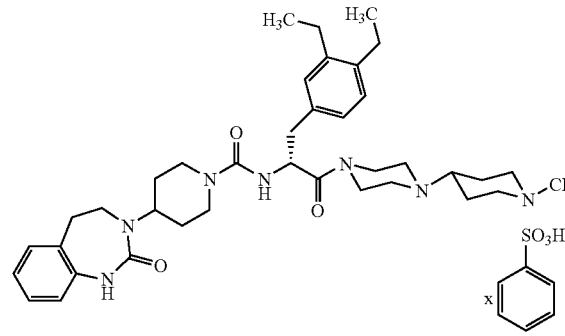

1.0 g (1.52 mmol) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide and 240 mg (1.52 mmol) benzenesulphonic acid are dissolved in 14 ml boiling isopropanol. The solution is stirred for 24 hours at 50° C. Then the temperature is reduced by 5° C. every 8 hours, during which time a white precipitate is formed. After 3 days and at a final temperature of 25° C. the solid formed is filtered off, washed with 5 ml isopropanol and dried for 12 hours at 50° C.

Yield: 580 mg (47% of theory)

Example 24

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-1,5-disulphonate (6d)

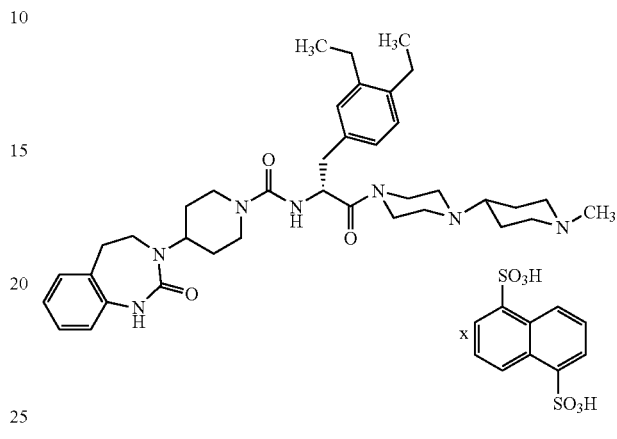

A solution of 1.427 g naphthalene-1,5-disulphonic acid (4.95 mmol) in 70 ml isopropanol is added to 3.25 g (4.94 mmol) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide and heated to 80° C. The now clear solution is cooled to ambient temperature, by lowering the temperature of the heating bath by 5° C. every 6 hours. The resultant suspension is filtered, the isolated solid is dried for 12 hours at 40° C.

Yield: 3.7 g (79% of theory)

Example 25

4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-2-sulphonate (6e)

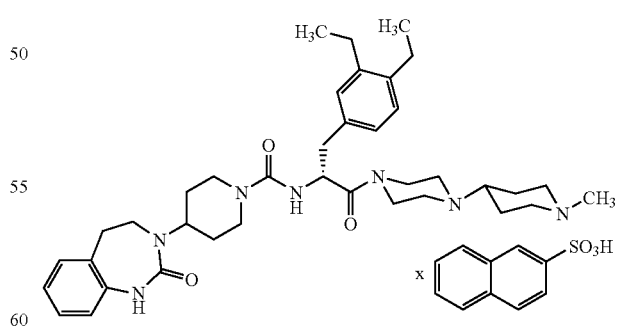

0.25 g (0.38 mmol) 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide and 86.2 mg (0.38 mmol) naphthalene-2-sulphonic acid monohydrate are suspended in 5 ml isopropanol and refluxed. The solution is cooled to ambient temperature within 6 days in 5° C. stages and filtered. The isolated solid is washed with isopropanol and dried for 12 hours at 60° C.

Yield: 150 mg (46% of theory)

BRIEF DESCRIPTION OF THE FIGURES

FIG. 1 shows the X-ray powder diffractogram of the crystalline compound 1-[4-amino-3,5-dibromo-N-[[4-(2,3,4,5-tetrahydro-2(1H)-oxo-1,3-benzodiazepin-3-yl)-1-piperidinyl]-carbonyl]-D-phenylalanyl]-4-(1-piperidinyl)-piperidine-p-toluenesulphonate (1a).

FIG. 2 shows the X-ray powder diffractogram of the crystalline compound 1-[4-amino-3,5-dibromo-N-[[4-(2,3,4,5-tetrahydro-2(1H)-oxo-1,3-benzodiazepin-3-yl)-1-piperidinyl]-carbonyl]-D-phenylalanyl]-4-(1-piperidinyl)-piperidine-benzenesulphonate (1b).

FIG. 3 shows the X-ray powder diffractogram of the crystalline compound 1-[4-amino-3,5-dibromo-N-[[4-(2,3,4,5-tetrahydro-2(1H)-oxo-1,3-benzodiazepin-3-yl)-1-piperidinyl]-carbonyl]-D-phenylalanyl]-4-(1-piperidinyl)-piperidine-maleate (1c).

FIG. 4 shows the X-ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dimaleate (2a).

FIG. 5 shows the X-ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrobromide (2b).

FIG. 6 shows the X-ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dihydrobromide (2c).

FIG. 7 shows the X-ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrochloride (2d).

FIG. 8 shows the X-ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate difumarate (2e).

FIG. 9 shows the X-ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate disuccinate (2f).

FIG. 10 shows the X-ray powder diffractogram of the crystalline compound (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate sulphate (2g).

FIG. 11a shows the X-ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrobromide (3a)—polymorph 1.

FIG. 11b shows the X-ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrobromide (3a)—polymorph 2.

FIG. 12a shows the X-ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrochloride (3b)—polymorph 1.

FIG. 12b shows the X-ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrochloride (3b)—polymorph 2.

FIG. 13 shows the X-ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate phosphate (3c).

FIG. 14 shows the X-ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2R,3R)-2,3-dihydroxybutanedioate (3d).

FIG. 15 shows the X-ray powder diffractogram of the crystalline compound 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2S,3S)-2,3-dihydroxybutanedioate (3e).

FIG. 16 shows the X-ray powder diffractogram of the crystalline compound (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate fumarate (4a).

FIG. 17 shows the X-ray powder diffractogram of the crystalline compound (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate sulphate (4b).

FIG. 18 shows the X-ray powder diffractogram of the crystalline compound (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrochloride-pentahydrate (5a).

FIG. 19 shows the X-ray powder diffractogram of the crystalline compound (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-(2S,3S)-2,3-dihydroxybutanedioate (5b).

FIG. 20 shows the X-ray powder diffractogram of the crystalline compound (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrobromide-pentahydrate (5c).

FIG. 21 shows the X-ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-dimaleate (6a).

FIG. 22 shows the X-ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-p-toluenesulphonate (6b).

FIG. 23 shows the X-ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-benzenesulphonate (6c).

FIG. 24 shows the X-ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-1,5-disulphonate (6d).

FIG. 25 shows the X-ray powder diffractogram of the crystalline compound 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-2-sulphonate (6e).

What is claimed is:

1. A crystalline form of 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine-p-toluenesulphonate which, when subjected to X-ray powder diffraction, exhibits a characteristic diffraction pattern which yields the following calculated values for d (the interplanar spacing between the atoms in the crystal): 19.49 Å, 12.16 Å, 6.46 Å, 6.08 Å, 5.4 Å, 5.17 Å and 3.82 Å.

2. A crystalline form of 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine-benzenesulphonate (1b), which, when subjected to X-ray powder diffraction, exhibits a characteristic diffraction pattern which yields the following calculated values for d (the interplanar spacing between the atoms in the crystal): 17.6 Å, 12.29 Å, 7.24 Å, 5.84 Å and 5.34 Å.

3. A crystalline form of 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine-maleate (1c), which, when subjected to X-ray powder diffraction, exhibits a characteristic diffraction pattern which yields the following calculated values for d (the interplanar spacing between the atoms in the crystal): 16.14 Å, 11.7 Å, 6.3 Å, 5.04 Å, 4.61 Å, 4.43 Å, 4.03 Å and 3.8 Å.

4. A crystalline form of (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dimaleate (2a), which, when subjected to X-ray powder diffraction, exhibits a characteristic diffraction pattern which yields the following calculated values for d (the interplanar spacing between the atoms in the crystal): 7.92 Å, 5.45 Å, 5.29 Å, 4.99 Å, 4.66 Å and 4.45 Å.

5. A crystalline form of (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrobromide (2b), which, when subjected to X-ray powder diffraction, exhibits a characteristic diffraction pattern which yields the following calculated values for d (the interplanar spacing between the atoms in the crystal): 4.71 Å, 4.49 Å, 4.39 Å, 3.77 Å, 3.71 Å and 3.45 Å.

6. A crystalline form of (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate dihydrobromide (2c), which, when subjected to X-ray powder diffraction, exhibits a characteristic diffraction pattern which yields the following calculated values for d (the interplanar spacing between the atoms in the crystal): 21.69 Å, 5.81 Å, 4.74 Å, 4.63 Å, 4.15 Å and 3.78 Å.

7. A crystalline form of (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate hydrochloride (2d), which, when subjected to X-ray powder diffraction, exhibits a characteristic diffraction pattern which yields the following calculated values for d (the interplanar spacing between the atoms in the crystal): 7.59 Å, 5.78 Å, 4.95 Å, 4.69 Å, 4.59 Å, 4.12 Å and 3.73 Å.

8. A crystalline form of (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate difumarate (2e), which, when subjected to X-ray powder diffraction, exhibits a characteristic diffraction pattern which yields the following calculated values for d (the interplanar spacing between the atoms in the crystal): 8.16 Å, 6.29 Å, 5.21 Å, 4.63 Å, 4.37 Å and 3.72 Å.

9. A crystalline form of (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate disuccinate (2f), which, when subjected to X-ray powder diffraction, exhibits a characteristic diffraction pattern which yields the following calculated values for d (the interplanar spacing between the atoms in the crystal): 8.18 Å, 6.46 Å, 5.26 Å, 5.18 Å, 4.61 Å and 4.32 Å.

10. A crystalline form of (R)-1-(4-amino-3-chloro-5-trifluoromethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate sulphate (2g), which, when subjected to X-ray powder diffraction, exhibits a characteristic diffraction pattern which yields the following calculated values for d (the interplanar spacing between the atoms in the crystal): 5.98 Å, 5.78 Å, 5.37 Å, 4.24 Å and 4.02 Å.

11. A crystalline form of 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrobromide (3a, polymorph 1), which, when subjected to X-ray powder diffraction, exhibits a characteristic diffraction pattern which yields the following calculated values for d (the interplanar spacing between the atoms in the crystal): 7.86 Å, 6.18 Å, 5.81 Å, 4.66 Å and 4.06 Å.

12. A crystalline form of 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrobromide (3a, polymorph 2), which, when subjected to X-ray powder diffraction, exhibits a characteristic diffraction pattern which yields the following calculated values for d (the interplanar spacing between the atoms in the crystal): 25.99 Å, 7.73 Å, 7.10 Å, 6.05 Å, 5.89 Å, 4.28 Å and 3.92 Å.

13. A crystalline form of 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrochloride (3b, polymorph 1), which, when subjected to X-ray powder diffraction, exhibits a characteristic diffraction pattern which yields the following calculated values for d (the interplanar spacing between the atoms in the crystal): 7.68 Å, 6.15 Å, 5.79 Å, 4.64 Å, 4.15 Å and 4.03 Å.

14. A crystalline form of 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate hydrochloride (3b, polymorph 2), which, when subjected to X-ray powder diffraction, exhibits a characteristic diffraction pattern which yields the following calculated values for d (the interplanar spacing between the atoms in the crystal): 7.74 Å, 7.13 Å, 6.00 Å, 5.88 Å and 4.22 Å.

15. A crystalline form of 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate phosphate (3c), which, when subjected to X-ray powder diffraction, exhibits a characteristic diffraction pattern which yields the following calculated values for d (the interplanar spacing between the atoms in the crystal): 8.90 Å, 5.53 Å, 5.15 Å, 4.83 Å and 4.63 Å.

16. A crystalline form of 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2R,3R)-2,3-dihydroxybutanedioate (3d), which, when subjected to X-ray powder diffraction, exhibits a characteristic diffraction pattern which yields the following calculated values for d (the interplanar spacing between the atoms in the crystal): 10.02 Å, 8.90 Å, 5.54 Å, 5.20 Å, 4.88 Å and 4.67 Å.

17. A crystalline form of 4-(1,2,4,5-tetrahydro-2-oxo-3H-1,3-benzodiazepin-3-yl)-(1R)-1-[(4-hydroxy-3,5-dimethylphenyl)methyl]-2-[4-(4-morpholinyl)-1-piperidinyl]-2-oxoethyl 1-piperidinecarboxylate (2S,3S)-2,3-dihydroxybutanedioate (3e), which, when subjected to X-ray powder diffraction, exhibits a characteristic diffraction pattern which yields the following calculated values for d (the interplanar spacing between the atoms in the crystal): 8.97 Å, 5.57 Å, 5.17 Å, 4.87 Å and 4.65 Å.

18. A crystalline form of (R)-1-(4-hydroxy-3,5-dimethylbenzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate fumarate (4a), which, when subjected to X-ray powder diffraction, exhibits a characteristic diffraction pattern which yields the following calculated values for d (the interplanar spacing between the atoms in the crystal): 9.01 Å, 6.30 Å, 5.26 Å, 5.07 Å, 4.72 Å and 4.52 Å.

19. A crystalline form of (R)-1-(4-hydroxy-3,5-dimethylbenzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate sulphate (4b), which, when subjected to X-ray powder diffraction, exhibits a characteristic diffraction pattern which yields the following calculated values for d (the interplanar spacing between the atoms in the crystal): 12.79 Å, 10.80 Å, 5.23 Å, 4.65 Å and 4.18 Å.

20. A crystalline form of (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrochloride-pentahydrate (5a), which, when subjected to X-ray powder diffraction, exhibits a characteristic diffraction pattern which yields the following calculated values for d (the interplanar spacing between the atoms in the crystal):=7.29 Å, 7.2 Å, 5.84 Å, 4.42 Å and 4.11 Å.

21. A crystalline form of (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-(2S,3S)-2,3-dihydroxybutanedioate (5b), which, when subjected to X-ray powder diffraction, exhibits a characteristic diffraction pattern which yields the following calculated values for d (the interplanar spacing between the atoms in the crystal): 10.21 Å, 5.67 Å, 4.7 Å, 4.51 Å and 4.14 Å.

22. A crystalline form of (S)-2-(4-amino-3-chloro-5-trifluoromethyl-benzyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione-hydrobromide-pentahydrate (5c), which, when subjected to X-ray powder diffraction, exhibits a characteristic diffraction pattern which yields the following calculated values for d (the interplanar spacing between the atoms in the crystal): 7.22 Å, 5.83 Å, 4.65 Å, 4.52 Å, 4.12 Å and 3.75 Å.

23. A crystalline form of 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-dimaleate (6a), which, when subjected to X-ray powder diffraction, exhibits a characteristic diffraction pattern which yields the following calculated values for d (the interplanar spacing between the atoms in the crystal): 21.21 Å, 9.99 Å, 5.52 Å, 5.33 Å, 4.81 Å and 3.99 Å.

24. A crystalline form of 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-p-toluenesulphonate (6b), which, when subjected to X-ray powder diffraction, exhibits a characteristic diffraction pattern which yields the following calculated values for d (the interplanar spacing between the atoms in the crystal): 25.57 Å, 8.59 Å, 7.61 Å, 7.04 Å, 6.19 Å and 5.25 Å.

25. A crystalline form of 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-benzenesulphonate (6c), which, when subjected to X-ray powder diffraction, exhibits a characteristic diffraction pattern which yields the following calculated values for d (the interplanar spacing between the atoms in the crystal): 10.53 Å, 6.68 Å, 5.87 Å, 5.10 Å and 5.00 Å.

26. A crystalline form of 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-1,5-disulphonate (6d), which, when subjected to X-ray powder diffraction, exhibits a characteristic diffraction pattern which yields the following calculated values for d (the interplanar spacing between the atoms in the crystal): 8.47 Å, 7.15 Å, 6.95 Å, 5.29 Å, 4.41 Å, 4.07 Å and 3.47 Å.

27. A crystalline form of 4-(2-oxo-1,2,4,5-tetrahydro-1,3-benzodiazepin-3-yl)-piperidine-1-carboxylic acid-{(R)-1-(3,4-diethyl-benzyl)-2-[4-(1-methyl-piperidin-4-yl)-piperazin-1-yl]-2-oxo-ethyl}-amide-naphthalene-2-sulphonate (6e), which, when subjected to X-ray powder diffraction, exhibits a characteristic diffraction pattern which yields the following calculated values for d (the interplanar spacing between the atoms in the crystal): 9.93 Å, 8.75 Å, 8.22 Å, 7.43 Å, 6.21 Å, 4.42 Å and 4.23 Å.

* * * * *